United States Patent
Pallikaris et al.

(10) Patent No.: US 7,004,953 B2
(45) Date of Patent: Feb. 28, 2006

(54) DEVICE FOR SEPARATING THE EPITHELIUM LAYER FROM THE SURFACE OF THE CORNEA OF AN EYE

(75) Inventors: Ioannis Pallikaris, Heraklion (GR); Harilaos S. Ginis, Heraklion (GR)

(73) Assignee: FOS Holding S.A., Luxembourg (LU)

(*) Notice: Subject to any disclaimer, the term of this patent is extended or adjusted under 35 U.S.C. 154(b) by 0 days.

(21) Appl. No.: 10/098,167

(22) Filed: Mar. 12, 2002

(65) Prior Publication Data

US 2003/0018348 A1 Jan. 23, 2003

Related U.S. Application Data

(63) Continuation-in-part of application No. 09/911,356, filed on Jul. 23, 2001.

(51) Int. Cl.
*A61F 9/00* (2006.01)

(52) U.S. Cl. ...................... 606/166; 604/294

(58) Field of Classification Search ............... 606/166, 606/167, 5, 6; 604/296
See application file for complete search history.

(56) References Cited

U.S. PATENT DOCUMENTS

| | | | |
|---|---|---|---|
| 2,881,500 A | 4/1959 | Furness | |
| 4,198,132 A | 4/1980 | Seger et al. | |
| 4,346,482 A | 8/1982 | Tennant et al. | |
| 4,381,007 A | 4/1983 | Doss | |
| 4,417,579 A | 11/1983 | Soloviev et al. | |
| 4,534,827 A * | 8/1985 | Henderson | 216/101 |
| 4,646,720 A | 3/1987 | Peyman et al. | |
| 4,659,584 A | 4/1987 | Schilk | |
| 4,662,370 A | 5/1987 | Hoffmann et al. | |
| 4,662,881 A | 5/1987 | Nordan | |
| 4,665,914 A | 5/1987 | Tanne | |
| 4,676,790 A | 6/1987 | Kern | |
| 4,688,570 A | 8/1987 | Kramer et al. | |
| 4,715,858 A | 12/1987 | Lindstrom | |
| 4,770,172 A | 9/1988 | L'Esperance, Jr. | |
| 4,773,414 A | 9/1988 | L'Esperance, Jr. | |
| 4,775,361 A | 10/1988 | Jacques et al. | |
| 4,793,344 A | 12/1988 | Cumming et al. | |
| 4,798,204 A | 1/1989 | L'Esperance, Jr. | |
| 4,838,266 A | 6/1989 | Koziol et al. | |
| 4,840,175 A | 6/1989 | Peyman | |

(Continued)

FOREIGN PATENT DOCUMENTS

CA 2355478 A1 2/2002

(Continued)

OTHER PUBLICATIONS

Terry J. Van Der Werff, D.Phil., *A New Single-Parameter Ocular Rigidity Function*, vol. 92, pp. 391-395 (1981).

(Continued)

*Primary Examiner*—Julian W. Woo
*Assistant Examiner*—Victor X. Nguyen
(74) *Attorney, Agent, or Firm*—Brinks Hofer Gilson & Lione

(57) ABSTRACT

A device is disclosed for separating the epithelial layer of a cornea from the eye. The device includes a separator having an edge to remove the epithelial layer as the separator moves across the eye. The edge includes a thickness thicker than the thickness of at least one epithelial cell and less thick than the thickness of the epithelial layer. Separation can be performed mechanically, without the use of chemicals, so that the shape and integrity of the separated epithelial layer is preserved. The device can also be used with a polymer film that adheres to the epithelial layer to help preserve an integrity of the epithelial layer.

167 Claims, 14 Drawing Sheets

U.S. PATENT DOCUMENTS

| | | |
|---|---|---|
| 4,844,060 A | 7/1989 | Krumeich |
| 4,865,033 A | 9/1989 | Krumeich et al. |
| 4,884,570 A | 12/1989 | Krumeich et al. |
| 4,955,894 A * | 9/1990 | Herman .................. 606/167 |
| 5,011,498 A | 4/1991 | Krumeich et al. |
| 5,108,388 A | 4/1992 | Trokel |
| 5,108,412 A | 4/1992 | Krumeich et al. |
| 5,133,726 A | 7/1992 | Ruiz et al. |
| 5,171,318 A | 12/1992 | Gibson et al. |
| 5,192,316 A | 3/1993 | Ting |
| 5,196,027 A | 3/1993 | Thompson et al. |
| 5,213,720 A | 5/1993 | Civerchia |
| 5,215,104 A * | 6/1993 | Steinert .................. 128/898 |
| 5,279,611 A | 1/1994 | McDonnell et al. |
| 5,312,330 A | 5/1994 | Klopotek |
| 5,312,413 A * | 5/1994 | Eaton et al. ............. 606/107 |
| 5,318,047 A | 6/1994 | Davenport et al. |
| 5,319,424 A | 6/1994 | Tomiyama |
| 5,323,788 A | 6/1994 | Silvestrini et al. |
| 5,374,515 A | 12/1994 | Parenteau et al. |
| 5,395,385 A * | 3/1995 | Kilmer et al. ............. 606/166 |
| 5,423,801 A | 6/1995 | Marshall et al. |
| 5,437,658 A | 8/1995 | Muller et al. |
| 5,462,739 A | 10/1995 | Dan et al. |
| 5,490,849 A | 2/1996 | Smith |
| 5,492,135 A * | 2/1996 | DeVore et al. ............ 128/898 |
| 5,496,339 A | 3/1996 | Koepnick |
| 5,505,723 A | 4/1996 | Muller |
| 5,522,888 A | 6/1996 | Civerchia |
| 5,549,597 A | 8/1996 | Shimmick et al. |
| 5,549,632 A | 8/1996 | Lai |
| 5,554,155 A | 9/1996 | Awh et al. |
| 5,599,341 A | 2/1997 | Mathis et al. |
| 5,613,965 A | 3/1997 | Muller |
| 5,630,810 A | 5/1997 | Machat |
| 5,632,757 A | 5/1997 | Arnott |
| 5,647,865 A | 7/1997 | Swinger |
| 5,649,943 A | 7/1997 | Amoils |
| 5,658,303 A | 8/1997 | Koepnick |
| 5,676,679 A * | 10/1997 | Simon et al. .............. 606/170 |
| 5,685,998 A | 11/1997 | Shannon et al. |
| 5,690,657 A | 11/1997 | Koepnick |
| 5,699,810 A | 12/1997 | Pallikaris |
| 5,700,274 A * | 12/1997 | Feaster .................. 606/167 |
| 5,711,762 A | 1/1998 | Trokel |
| 5,716,633 A | 2/1998 | Civerchia |
| 5,722,427 A | 3/1998 | Wakil et al. |
| 5,722,971 A | 3/1998 | Peyman |
| 5,735,843 A | 4/1998 | Trokel |
| 5,740,803 A | 4/1998 | Gray et al. |
| 5,741,245 A | 4/1998 | Cozean et al. |
| 5,779,696 A | 7/1998 | Berry et al. |
| 5,795,351 A | 8/1998 | Clapham |
| 5,807,380 A | 9/1998 | Dishler |
| 5,807,381 A * | 9/1998 | Lieberman .................. 606/5 |
| 5,827,641 A | 10/1998 | Parenteau et al. |
| 5,833,701 A | 11/1998 | Gordon |
| RE35,974 E | 12/1998 | Davenport et al. |
| 5,851,213 A | 12/1998 | Berleth et al. |
| 5,857,995 A * | 1/1999 | Thomas et al. ............. 604/22 |
| 5,904,678 A | 5/1999 | Pop |
| 5,919,185 A | 7/1999 | Peyman |
| 5,941,874 A | 8/1999 | Hohla |
| 5,964,748 A | 10/1999 | Peyman |
| 5,970,984 A | 10/1999 | Wakil et al. |
| 5,975,351 A | 11/1999 | DeLacerda |
| 5,980,543 A | 11/1999 | Carriazo et al. |
| 5,984,916 A | 11/1999 | Lai |
| 5,989,272 A | 11/1999 | Barron et al. |
| 5,997,559 A | 12/1999 | Ziemer |
| 6,006,756 A | 12/1999 | Shadduck |
| 6,030,398 A | 2/2000 | Klopotek |
| 6,036,683 A | 3/2000 | Jean et al. |
| 6,071,293 A | 6/2000 | Krumeich |
| 6,083,236 A | 7/2000 | Feingold |
| 6,099,541 A | 8/2000 | Klopotek |
| 6,110,202 A | 8/2000 | Barraquer et al. |
| 6,126,668 A | 10/2000 | Bair et al. |
| 6,129,723 A | 10/2000 | Anderson et al. |
| 6,132,421 A | 10/2000 | Clapham |
| 6,162,210 A | 12/2000 | Shadduck |
| 6,171,336 B1 | 1/2001 | Sawusch |
| 6,187,053 B1 | 2/2001 | Minuth |
| 6,203,538 B1 | 3/2001 | Peyman |
| 6,217,571 B1 | 4/2001 | Peyman |
| 6,221,067 B1 | 4/2001 | Peyman |
| 6,241,721 B1 | 6/2001 | Cozean et al. |
| 6,254,619 B1 * | 7/2001 | Garabet et al. ............. 606/166 |
| 6,264,648 B1 | 7/2001 | Peyman |
| 6,280,435 B1 | 8/2001 | Odrich et al. |
| 6,280,469 B1 | 8/2001 | Terry et al. |
| 6,280,470 B1 | 8/2001 | Peyman |
| 6,293,938 B1 | 9/2001 | Muller et al. |
| 6,302,896 B1 | 10/2001 | Carriazo et al. |
| 6,306,075 B1 | 10/2001 | Shadduck |
| 6,322,216 B1 | 11/2001 | Yee et al. |
| 6,331,177 B1 | 12/2001 | Munnerlyn et al. |
| 6,335,006 B1 | 1/2002 | Miller |
| 6,379,370 B1 * | 4/2002 | Feinsod .................. 606/166 |
| 6,391,055 B1 | 5/2002 | Ikada et al. |
| 6,409,345 B1 | 6/2002 | Molebny et al. |
| 6,436,093 B1 | 8/2002 | Ruiz et al. |
| 6,451,039 B1 | 9/2002 | Richey, Jr. et al. |
| 6,458,141 B1 | 10/2002 | Peyman |
| 6,464,692 B1 | 10/2002 | Ruiz et al. |
| 6,497,701 B1 | 12/2002 | Shimmick et al. |
| 6,506,198 B1 | 1/2003 | Amano |
| 6,530,916 B1 | 3/2003 | Shimmick |
| 6,543,453 B1 | 4/2003 | Klima et al. |
| 6,544,286 B1 | 4/2003 | Perez |
| 6,551,307 B1 | 4/2003 | Peyman |
| 6,589,558 B1 | 7/2003 | Pallikaris |
| 6,599,305 B1 | 7/2003 | Feingold |
| 6,607,527 B1 | 8/2003 | Ruiz et al. |
| 6,623,497 B1 | 9/2003 | Feingold |
| 6,626,924 B1 | 9/2003 | Klopotek |
| 6,638,271 B1 | 10/2003 | Munnerlyn et al. |
| 6,666,855 B1 | 12/2003 | Yee et al. |
| 6,673,062 B1 | 1/2004 | Yee et al. |
| 6,702,807 B1 | 3/2004 | Peyman |
| 6,702,832 B1 | 3/2004 | Ross et al. |
| 6,706,036 B1 | 3/2004 | Lai |
| 6,730,073 B1 | 5/2004 | Bruce |
| 2001/0053917 A1 | 12/2001 | Lin et al. |
| 2002/0026101 A1 | 2/2002 | Bookwalter |
| 2002/0026240 A1 | 2/2002 | Pallikaris et al. |
| 2002/0052596 A1 | 5/2002 | Pallikaris et al. |
| 2002/0052614 A1 | 5/2002 | GeBauer |
| 2002/0077640 A1 | 6/2002 | Metzger |
| 2003/0001847 A1 | 1/2003 | Pallikaris et al. |
| 2003/0011745 A1 | 1/2003 | Molebny et al. |
| 2003/0018348 A1 | 1/2003 | Pallikaris et al. |
| 2003/0105521 A1 | 6/2003 | Perez |
| 2003/0139755 A1 | 7/2003 | Dybbs |
| 2004/0059361 A1 | 3/2004 | Feingold |
| 2004/0073246 A1 | 4/2004 | Aufure et al. |
| 2004/0097955 A1 | 5/2004 | Feingold |

FOREIGN PATENT DOCUMENTS

| | | |
|---|---|---|
| DE | 027 50 492 A1 | 5/1979 |
| DE | 38 38 253 A1 | 5/1990 |
| DE | G93 15 396.1 U1 | 2/1994 |
| DE | 297 14 266 U1 | 12/1997 |

| | | |
|---|---|---|
| DE | 297 12 339 U1 | 1/1998 |
| DE | 298 05 538 U1 | 7/1998 |
| DE | 298 10 603 U1 | 12/1998 |
| DE | 198 47 089 A1 | 5/2000 |
| DE | 201 07 259 U1 | 12/2001 |
| DE | 201 15 585 U1 | 3/2002 |
| DE | 100 51 215 A1 | 5/2002 |
| DE | 101 19 477 A1 | 10/2002 |
| DE | 200 23 239 U1 | 8/2003 |
| DE | 202 04 635 U1 | 9/2003 |
| DE | 102 14 917 A1 | 10/2003 |
| DE | 102 32 169 A1 | 2/2004 |
| EP | 0 659 955 B1 | 1/1997 |
| EP | 0 873 735 A1 | 10/1998 |
| EP | 0 956 840 A2 | 11/1999 |
| EP | 1 114 628 A2 | 7/2001 |
| EP | 1 181 913 A2 | 2/2002 |
| EP | 1 199 055 A1 | 4/2002 |
| EP | 1 350 492 A2 | 10/2003 |
| FR | 2 691 625 A3 | 12/1993 |
| JP | 2002119532 A | 4/2002 |
| WO | WO 94/17851 A1 | 8/1994 |
| WO | WO 98/53774 A1 | 12/1998 |
| WO | WO 01/93791 A1 | 12/2001 |
| WO | WO 01/97729 A1 | 12/2001 |
| WO | WO 02/06883 A2 | 1/2002 |
| WO | WO 03/009789 A1 | 2/2003 |
| WO | WO 03/026542 A1 | 4/2003 |
| WO | WO 03/061518 A2 | 7/2003 |

OTHER PUBLICATIONS

Winston Roberts, M.D., and J. William Rogers, M.D., *Postural Effects on Pressure and Ocular Rigidity Measurements*, pp. 111-118 (Assumed published prior to filing date).

Peter P. Purslow, PhD, Wojciech S.S. Karwatowski, FROCOphth, *Ocular Elasticity*, pp. 1686-1692 (1996).

Joseph N. Simone, MD and Marc M. Whitacre, MD, *The Effect of Intraocular Gas and Fluid Volumes on Intraocular Pressure*, Ophthalmology, vol. 97, No. 2, pp. 238-243 (1990).

John E. Eisenlohr, M.E. Langham and A.E. Maumenee, *Manometric Studies of the Pressure-Volume Relationship in Living and Enucleated Eyes of Individual Human Subjects*, Brit. J. Ophthal., vol. 46, pp. 536-548 (1962).

Richard F. Brubaker, *Tonometry*, Clinical Ophthalmology, vol. 3, Chap. 47, pp. 1-7 (Assumed to be published before filing date).

Jonas S. Friedenwald, M.D., *Tonometer Calibration*, pp. 108-123 (1957).

Carsten Edmund, *Corneal Elasticity and Ocular Rigidity in Normal and Keratoconic Eyes*, Acta Ophthalmologica, vol. 66, pp. 134-140 (1988).

Ephraim Friedman, MD, Sara Krupsky, MD Anne Marie Lane, MPH, Setsuko S. Oak, Eric S. Friedman, MD, Kathleen Egan, MPH, Evangelos S. Gragoudas, MD, *Ocular Blood Flow Velocity in Age-Related Macular Degeneration*, Ophthalmology, vol. 102, No. 4, pp. 640-646 (1995).

Mark W, Johnson, MD, Dennis P. Han, MD, Kenneth E. Hoffman, MS, *The Effect of Scleral Buckling on Ocular Rigidity*, Ophthalmology, vol. 97, pp. 190-195 (1990).

Evangelos S. Gragoudas, MD, Suresh R. Chandra, MD, Ephraim Friedman, MD, Michael L. Klein, MD, Micael Van Buskirk, MD, *Disciform Degeneration of the Macula*, Arch Ophthalmol, vol. 94, pp. 755-757 (1976).

Ephraim Freidman, MD, *A Hemodynamic Model of the Pathogenesis of Age Related Macular Degeneration*, pp. 1-14 (1997).

Jeffrey B. Robin, MD *Overview of Microkeratomes*, (Assumed to be published before filing date).

Ioannis G. Pallikaris, MD, Maria E. Papatzanaki, MD, Evdoxia Z. Stathi, MD, Oliver Frenschock, and Anthimos Georgiadis, PhD, *Laser in Situ Keratomileusis*, Lasers in Surgery and Medicine, vol. 10 pp. 463-468, 1990.

Stephen L. Trokel, M.D., R. Srinivasan, PhD., and Bodil Baren, B.A., *Excimer Laser Surgery of the Cornea*, vol. 96, No. 6, pp. 710-715, 1983.

David S. Gartry, FRCS, FCOphth, Malcolm G. Kerr Muir, FRCS, FCOphth, John Marshall, PhD., *Photorefractive Keratectomy with an Argon Fluoride Excimer Laser: A Clinical Study*, vol. 7, pp. 420-435, Nov./Dec. 1991.

Lohmann, Chris P., MD, "Epi-Lasik Epi-Tome", presented Apr. 2004, Seville, Spain, 47 pages.

Photo using a light microscope of a blade manufactured by GeBauer, evaluated in Athens, Greece, on or about Jun. 2004, One page.

Soloway, Barrie., "US Clinical Studies with the Epik for E-Lasik" performed by Moria (Epi-Lasik and Lamellar Surgery), presented Sep. 18, 2004, Paris, France, Twenty-three pages.

Gebauer announcements of clinical results for the first 100 Epi-LASIK patients treated in Europe, Mar. 5, 2004, One page.

Chen, J-H. et al. "*Transportation of Adult Human Corneal Endothelium Ex Vivo: A Morphologic Study,*" Cornea 2001; vol. 20, No. 7: pp. 731-737.

Joo, C-K et al. "*Repopulation of Denuded Murine Descemet's Membrane with Life-Extended Murine Corneal Endothelial Cells as a Model for Corneal Cell Transplantation,* " Graefes Archive for Clinical and Experimental Ophthalmology 2000 ; vol. 238, No. 2: pp. 174-180.

Schwab, I. R. and Isseroff, R. R., "*Bioenginered Corneas—The Promise and the Challenge,*" New England Journal of Medicine 2000; vol. 343, No. 2: pp. 86-93.

Tsai, R. J-F. et al. "*Reconstruction of Damaged Corneas by Transplantation of Autologous Limbal Epithelial Cells*" New England Journal of Medicine 2000; vol. 343, No. 2: pp. 86-93.

Chen, C. C. et al. "*Human Corneal Epithelial Call Viability and Morphology after Dilute Alcohol Exposure*" Investigative Ophtomalogy & Visual Science 2002; vol. 43, No. 8, pp. 2593-2602.

Pallikaris, Ioannis G., M.D., et al. "*Epi-LASIK: Comparative Histological Evaluation of Mechanical and Alcohol-Assisted Epithelial Separation,*" J Cataract Refract Surg 2003; vol. 29:pp. 1493-1501.

EPI-Peeler Drawing by Geuder, Germany; No date Available, One page.

* cited by examiner

DEVICE FOR SEPARATING THE EPITHELIUM LAYER FROM THE SURFACE OF THE CORNEA OF AN EYE

REFERENCE TO EARLIER FILED APPLICATION

The present application is a continuation-in-part application of U.S. patent application Ser. No. 09/911,356, filed Jul. 23, 2001, the entire contents of which are incorporated by reference herein.

BACKGROUND

LASIK (Laser-Assisted In Situ Keratomileusis) is a surgical procedure intended to reduce a person's dependency on glasses or contact lenses. LASIK permanently changes the shape of the cornea, the clear covering of the front of the eye, using an excimer laser. A device, called a microkeratome, is used to cut a flap in the cornea. A hinge is left at one end of this flap. The flap is folded back revealing the stroma, the middle section of the cornea. Pulses from a computer-controlled laser vaporize a portion of the stroma and the flap is replaced. It is important that the knife used during the LASIK procedure is sharp, otherwise the quality of the procedure and the healing time are poor. Additionally the knife has to be sharp in order to produce consistent and reproducible flaps. There are some complications related to the use of microkeratomes. Common complications include the creation of an irregular flap, for example, a half flap, a buttonhole, or a total cup. These complications represent irregular incisions of the cornea, a situation that can permanently degrade visual performance.

Alternatively, PRK (Photo-Refractive Keratectomy) which is a technique developed earlier than LASIK may be used to correct the curvature of the cornea. In PRK a physician scrapes away the superficial layer, e.g., the epithelium, of the cornea. After the superficial layer is removed, laser treatment is applied on to the exposed surface of the cornea. A drawback of PRK, however, is that the healing period for the eye typically lasts for a week, much longer than the healing period of LASIK. Also, the patient experiences some pain during healing. Typically in PRK a disposable contact lens is used to cover the treated area of the cornea and help reduce postoperative pain.

In another technique, LASEK (Laser Epithelial Keratomileusis) the epithelial layer is separated from the surface of the cornea in a manner that the separated epithelial layer can be preserved. First, the epithelium is treated with and alcohol solution to partially devitalize it. Once the exact surface area of treatment is determined, a few drops of a weak alcohol solution is applied to the surface of the cornea and allowed to stay in contact with the epithelium for a few seconds. This weak alcohol solution is then rinsed off the surface of the eye. The function of the weak alcohol solution is to loosen the epithelial layer (50 microns) and to allow it to be peeled back in a sheet of epithelial cells, thereby exposing the underlying cornea. This is not to be confused with LASIK, which actually uses a microkeratome instrument to create a flap of both epithelium and the front part of the stromal tissue measuring anywhere between 130 to 180 microns.

In LASEK, the epithelium-only layer is laid back in a similar fashion to LASIK, but consists of only epithelium, not corneal stroma. Once the epithelial cells have been laid out of the way, the laser is applied to the surface of the cornea in the exact same fashion as in PRK. Once the laser treatment has been completed, the epithelial layer is laid back into place and a soft contact lens is placed over the eye as in PRK. The epithelial cells, which were partly devitalized by the weak alcohol solution, are laid over the treatment area and may serve as a facilitator of new epithelium healing underneath. The alcohol-devitalized epithelium falls off the eye, similar to a scab, in 5–10 days. These devitalized epithelial cells do not become the new surface of the eye, but simply serve as a protective agent in addition to the contact lens to facilitate comfort and healing of the new underlying epithelium. Alcohol treatment of the epithelium results in a severe amount of epithelial cell loss, a fact that may render the epithelial disk not usable, due to the reduced durability and adhesion on to the cornea.

Thus, there is a need for an automated corneal epithelium separator that addresses the above problems by separating the epithelial layer as a whole in a mechanical way, not chemical.

BRIEF SUMMARY

To help correct an imperfect vision of a patient's eye, an automated mechanical device separates the epithelial layer from the cornea of a patient's eye from the cornea. After the epithelial layer is separated from the cornea, a laser is used to help correct imperfections in the cornea. Thereafter, the epithelial layer is placed back on the cornea to reduce the visual rehabilitation period and reduce postoperative pain.

In one aspect, the device includes a separator such as a plate, wire or dull blade. The device can preserve a separated epithelial layer as a disk without rupturing the disk and without substantial epithelial cell loss. The epithelial layer is separated from the cornea without cutting the cornea.

The device includes a separator having an edge to remove the epithelial layer as the separator moves across the eye. The edge includes a thickness thicker than the thickness of at least one epithelial cell and less thick than the thickness of the epithelial layer.

DETAILED DESCRIPTION

To help correct an imperfect vision of a patient's eye, an automated mechanical device separates the epithelial layer from the cornea of a patient's eye from the cornea. A separator, such as a plate, wire or dull blade is used to separate the epithelial layer of the cornea from the basal membrane. In this way, the automated mechanical device can preserve the separated epithelial layer as a disk without rupturing the disk and without substantial epithelial cell loss, less than 5–10% loss, to ensure viability and stability of the epithelial disk after replacement on the surface of the cornea. After the epithelial layer is separated from the cornea, a laser is used to help correct imperfections in the cornea. Thereafter, the epithelial layer is placed back on the cornea to aid in the healing process of the eye.

Figure 1:
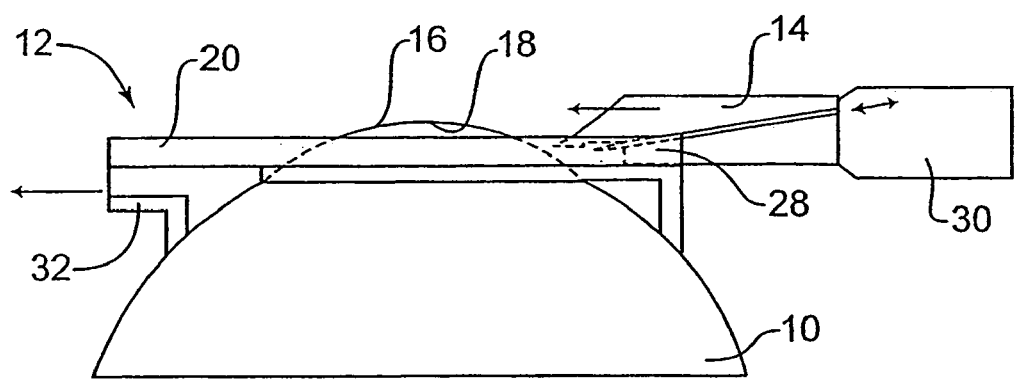
FIG. 1 is a diagram showing a side view of an eye and a epithelial separator with a separator located in a first position according to the preferred embodiments.

FIG. 1 is a diagram showing a side view of an eye 10 of a patient and a epithelial separator device 12. The epithelial separator device 12 includes a separator 14, shown here in a first position located away from the eye 10. The separator 14 includes a device that can scrape the epithelium from the cornea such as a plate, a wire or a knife with a dull edge. The separator 14 removes an epithelium layer 16 located above a corneal surface 18 of the eye 10. The separator 14 is not sharp enough to excise corneal tissue during operation of the epithelial separator device 12.

Figure 2:
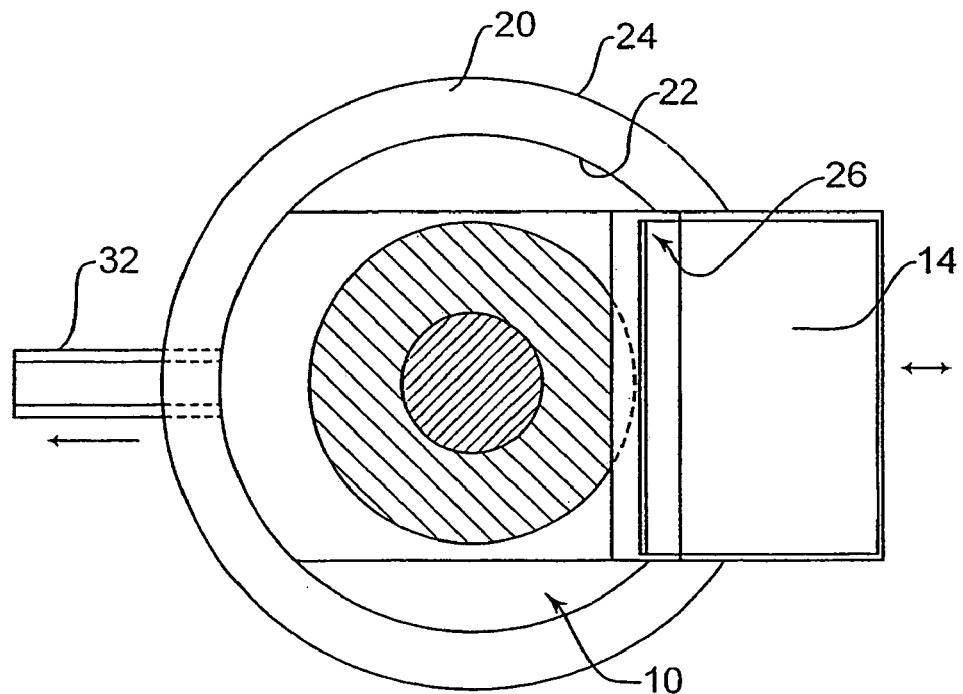
FIG. 2 is a diagram showing a top view of the eye and the separator located in a first position according to the preferred embodiments.

Referring also to FIG. 2, the epithelial separator device 12 includes a ring 20 that sits on the eye 10 with its plane parallel to a limbus of the eye. The ring 20 includes an internal diameter 22 ranging from about 10 to about 12 mm and external diameter 24 from about 13 to about 16 mm and including a groove 26 (best seen in FIG. 15). The groove 26 is dimensioned wider than the internal diameter 22. A separator support 28 fits in the groove 26 to carry the separator 14 on a determined travel.

An oscillation device 30 provides motion and vibration to the separator 14. The oscillation device 30 can oscillate the separator 14 either transversely or longitudinally with frequency ranging from about 10 Hz to about 10 KHz. Electromagnetic or piezoelectric forces on the separator 14 can provide the oscillation, or external rotating or vibrating wires can provide the oscillation. To maintain the ring 20 on the eye 10, for example during oscillation, the ring 20 can include a circumferential groove 32 positioned on a side of the eye 10. Suction can be applied to the circumferential groove 32 to ensure stable mounting of the ring 20 to the eye 10.

Figure 3:
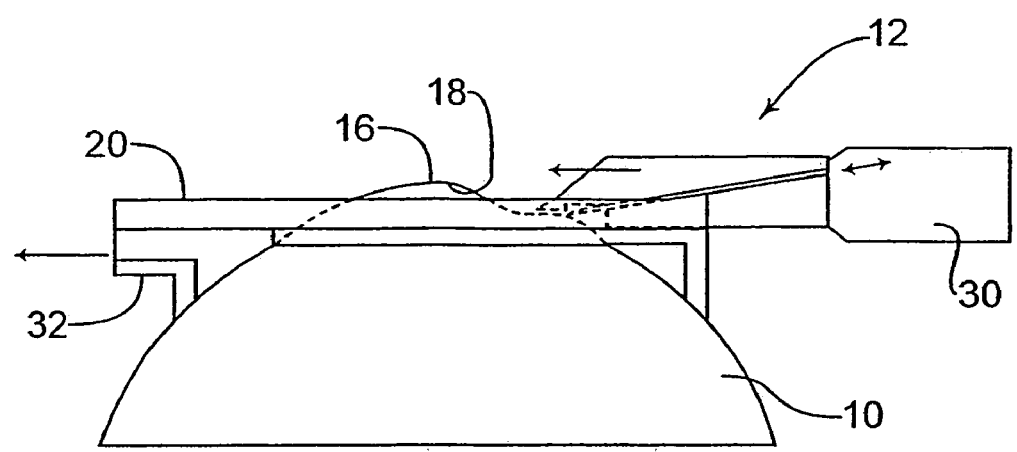
FIG. 3 is a diagram showing a side view of the eye and the separator located in a second position according to the preferred embodiments.
Figure 4:
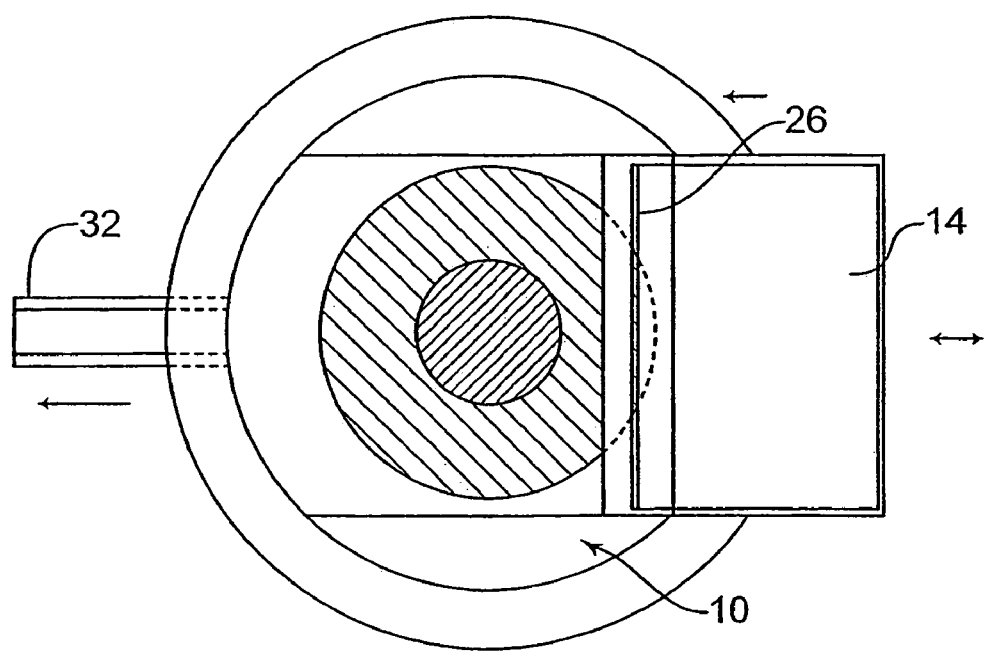
FIG. 4 is a diagram showing a top view of the eye and the separator located in a second position according to the preferred embodiments.
Figure 5:
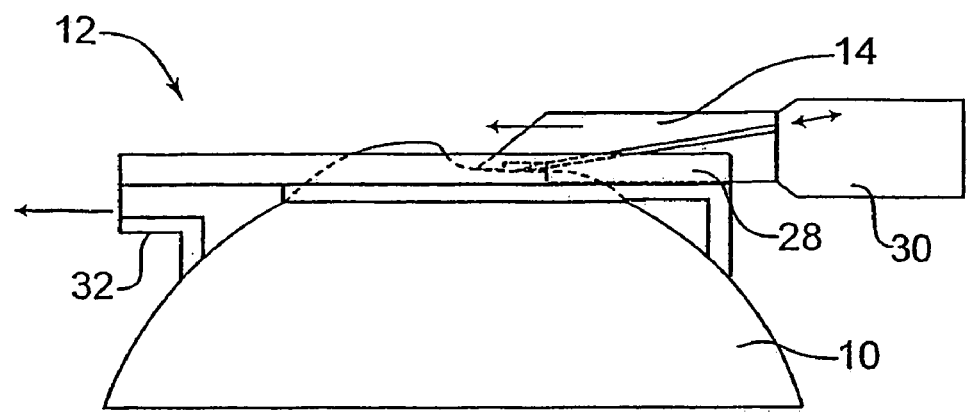
FIG. 5 is a diagram showing a side view of the eye and the separator located in a third position according to the preferred embodiments.
Figure 7:
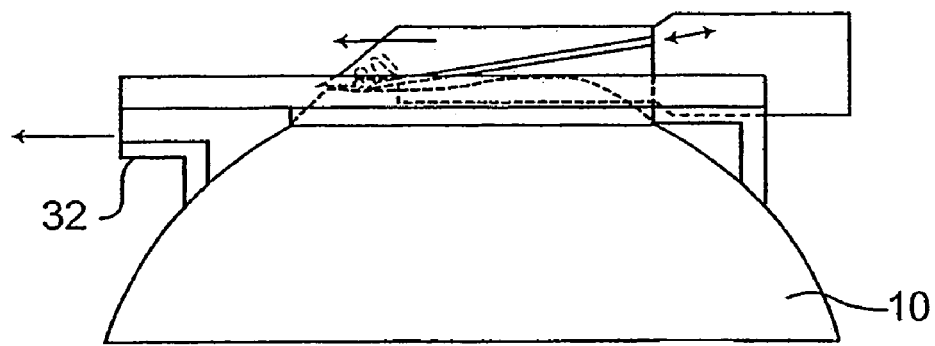
FIG. 7 is a diagram showing a side view of the eye and the separator located in a fourth position according to the preferred embodiments.

FIGS. 3 and 4 are diagrams showing a side and a top view, respectively, of the eye 10 and the separator 14 located in a second position with respect to the eye. As shown in FIGS. 3, 5 and 7, as the separator 14 travels to contact the eye 10, the corneal surface 18 is flattened. Such flattening is performed by an engagement surface that is positioned at a leading portion of the separator device 12. The flattening is performed prior to a portion of the epithelial layer being separated from the cornea. To accommodate the travel of the separator 14, the separator support 28 freely slides in the groove 26, for example, when driven by the oscillation device 30.

Figure 6:
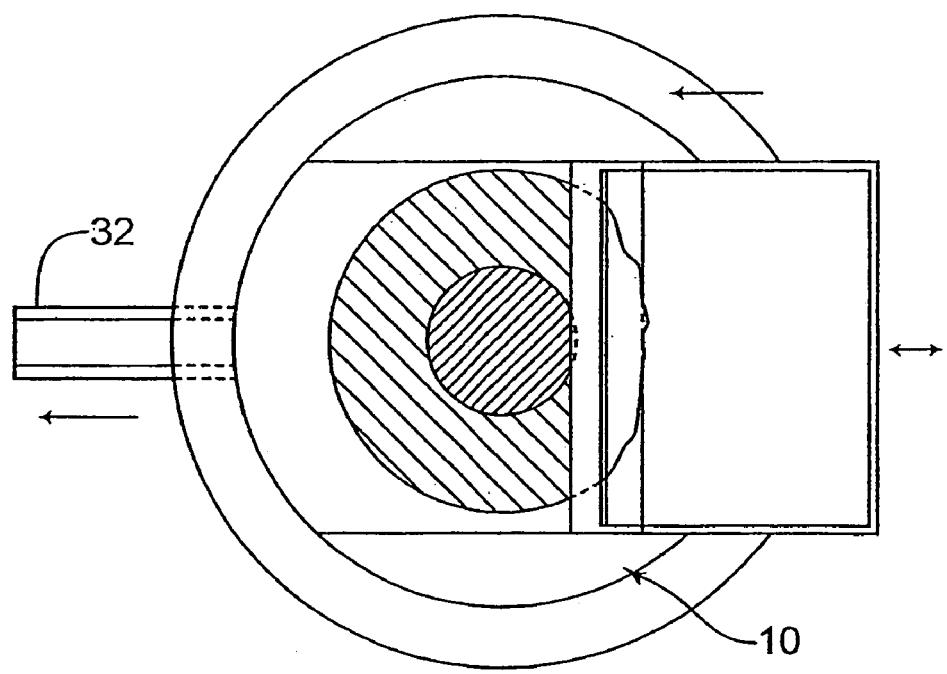
FIG. 6 is a diagram showing a top view of the eye and the separator located in a third position according to the preferred embodiments.

FIGS. 5 and 6 are diagrams showing a side and a top view of the eye 10 and the separator 14 located in a third position. As the separator 14 travels along the cornea 10, the epithelium layer 16 is separated from the cornea. The separator 14 separates the epithelium layer 16 without cutting the cornea 18.

Figure 8:
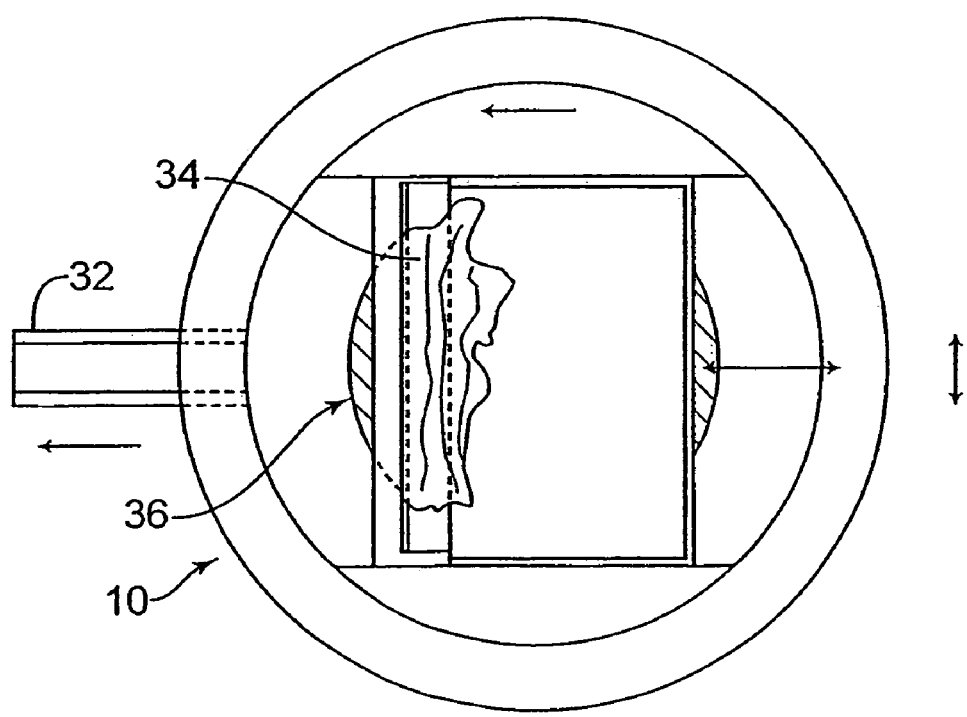
FIG. 8 is a diagram showing a top view of the eye and the separator located in a fourth position according to the preferred embodiments.

FIGS. 7 and 8 are diagrams showing a side and a top view of the eye 10 and the separator 14 located in a fourth position. In one embodiment, the travel of the separator 14 is controlled to produce an epithelial disk 34 hinged at an edge 36 of the epithelial disk 34. In another embodiment the epithelial disk 34 is completely detached for the corneal surface 18, for example, as described below.

Figure 9:
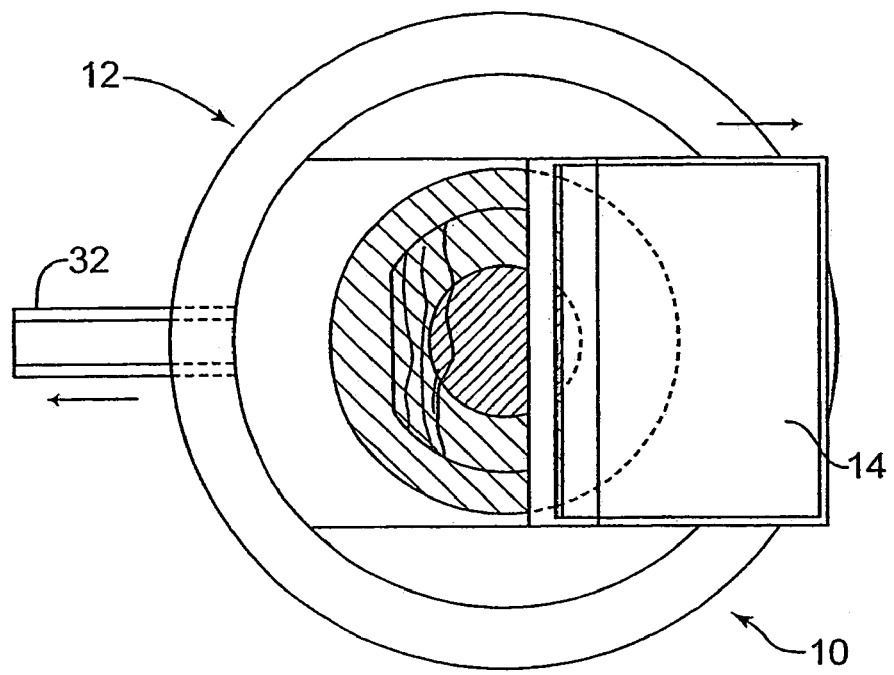
FIG. 9 is a diagram showing a top view of the eye and the separator located in a fifth position according to the preferred embodiments, the separator is retracted after epithelial separation.
Figure 10:
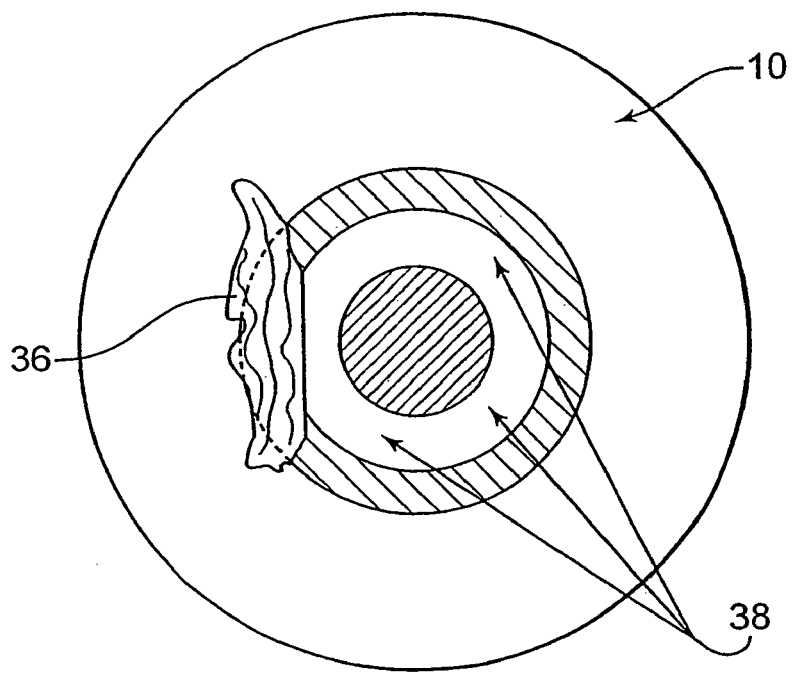
FIG. 10 is a diagram showing a top view of the eye with the separator removed.

FIG. 9 is a diagram showing a top view of the eye 10 and the separator 14 located in a retracted position after the epithelial disk 34 as been formed. After the separator 14 is retracted, suction to the circumferential groove 32 is turned off and the epithelial separator device 12 is removed from the eye 10. Referring also to FIG. 10, after the epithelial separator device 12 is removed, a deepithelialized area 38 is exposed that corresponds to a shape and size of the area that the separator 14 contacted during travel.

Figure 11:
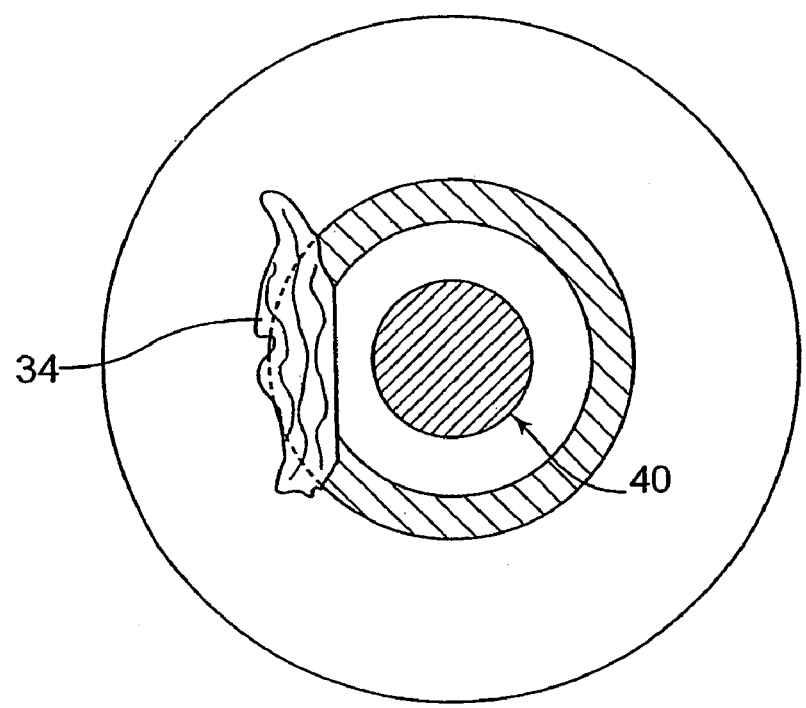
FIG. 11 is a diagram showing a top view of the eye after ablations is performed with a laser.
Figure 12:
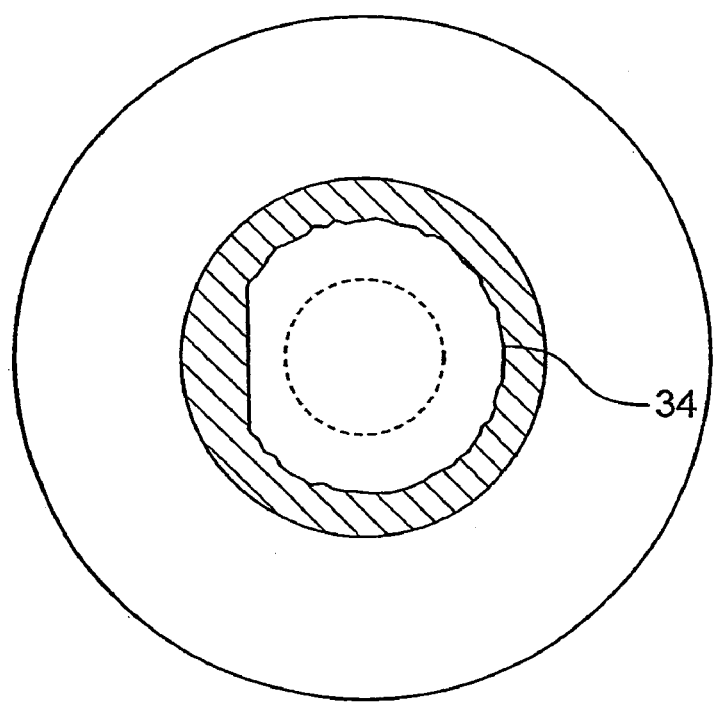
FIG. 12 is a diagram showing a top view of the eye with the epithelium replaced on the eye.
Figure 13:
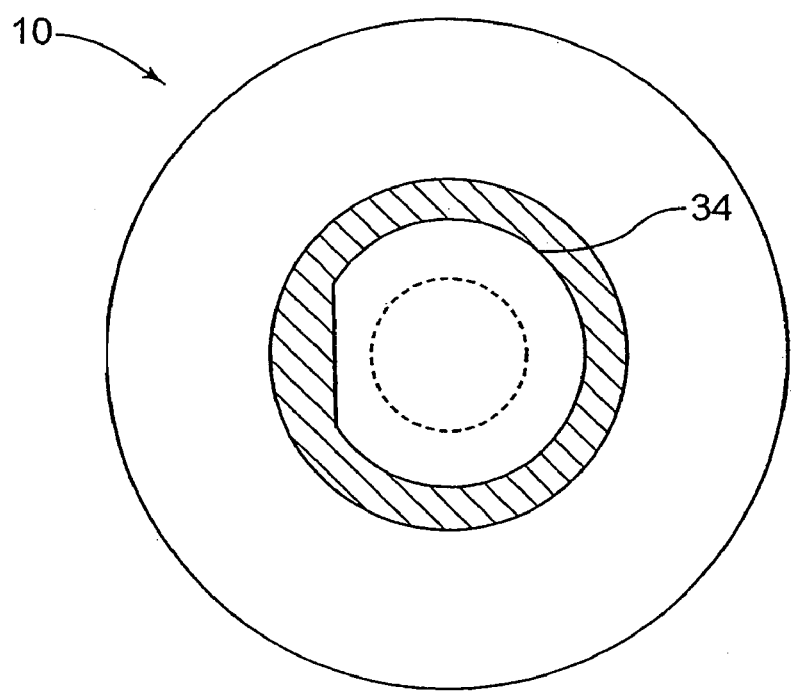
FIG. 13, is a diagram showing a top view of the eye with the epithelium smoothly stretched into place.

FIG. 11 shows a top view of the eye 10 after laser ablation is performed. The laser ablation forms an irradiated area 40 on the eye 10. Referring to FIG. 12, thereafter, the epithelium disk 34 is replaced on the corneal surface 18 of the eye 10 to aid in the healing process. Referring to FIG. 13, once replaced on the corneal surface 18, the epithelium disk 34 is preferably smoothly stretched into place.

Figure 14:
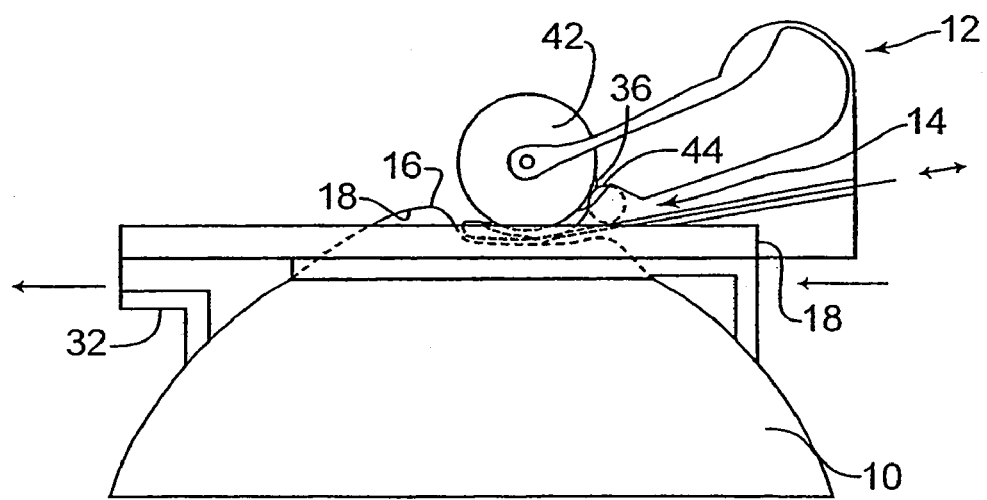
FIG. 14 is a diagram showing a side view of the eye and the epithelial separator device including a rotating drum.
Figure 15:
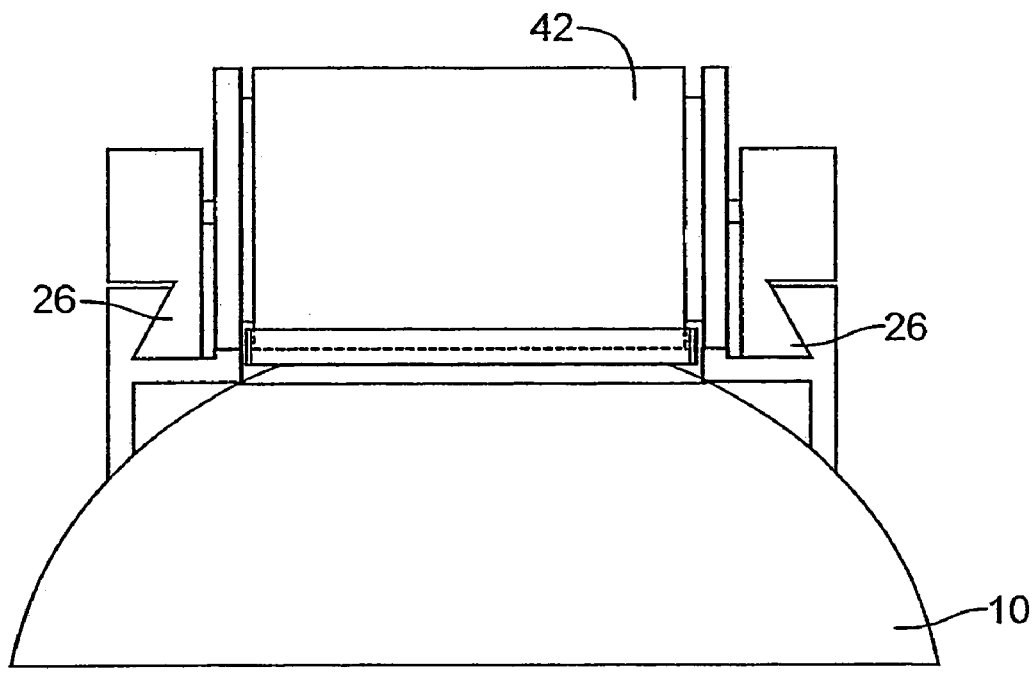
FIG. 15 is a diagram showing a front view of the eye and the epithelial separator device including the rotating drum.
Figure 16:
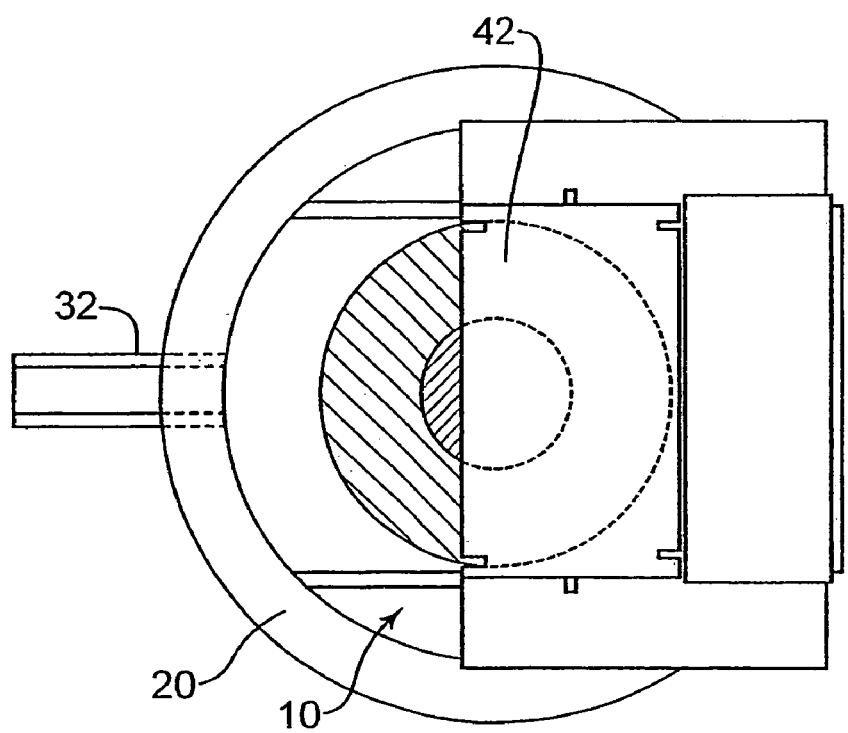
FIG. 16 is a diagram showing a top view of the eye and the epithelial separator device including the rotating drum.

FIG. 14 is a diagram showing a side view of the eye 10 and the epithelial separator device 12 including rotating drum 42. To rotate the drum 42, the epithelial separator device 12 may include a rotating gear 44. The gear 44 could also be used to provide movement to the separator support 28. Referring also to FIGS. 15 and 16, front and top views, respectively, of the epithelial separator device 12, the rotating gears 44 could be bilaterally placed on the separator support 28. The oscillating device 30 can provide for rotation of the gears 44 and the gears 44 can travel on rails, for example toothed rails, which run parallel to the groove 26.

Figure 17:
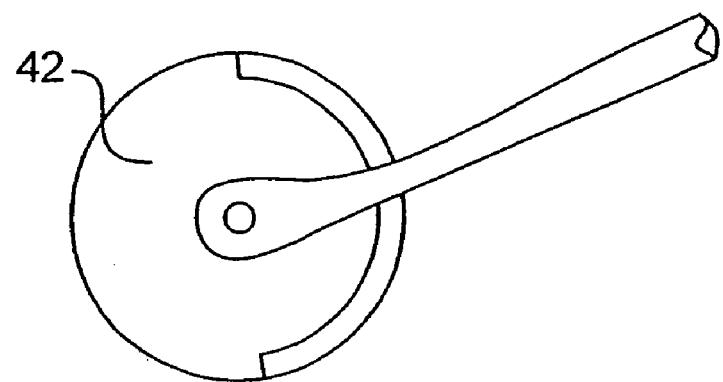
FIG. 17 is a diagram showing a drum according to one embodiment.

Since a typical thickness of an epithelial disk 36 includes about 50 microns, to preserve an epithelial disk 36, a separated epithelial disk 36 is rolled onto the drum 42. The drum 42 can include a diameter ranging from about 3 to about 9 mm and a length of about 12 mm. Referring also to FIG. 17, in one embodiment, to maintain integrity of the epithelial disk 36, the drum 42 can be coated with a hydrating and/or a conditioning substrate. The hydrating and/or conditioning substrate can include, for example, HEMA contact lenses, tissue culture media, silicone and biocompatible hydrogels. The hydrating and/or conditioning substrate can be removed from the drum after the epithelial disk 36 attaches on to the drum. Thereafter, the epithelial disk 36 can be removed from the drum 46 and replaced on the corneal surface 16, as described above.

Figure 18:
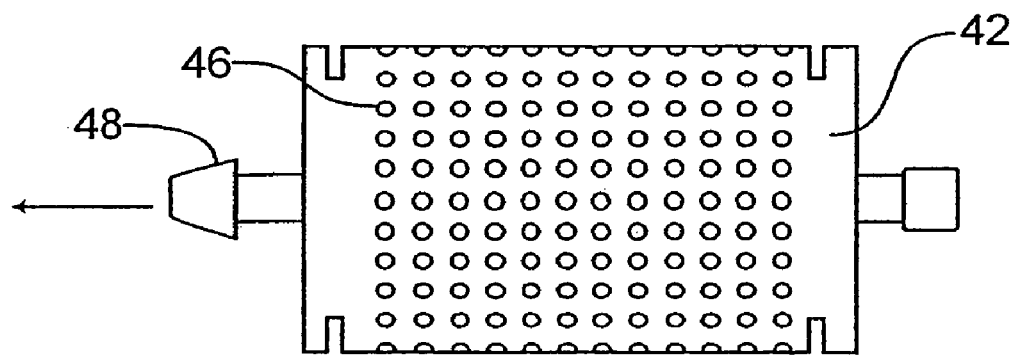
FIG. 18 is a diagram showing a drum according to another embodiment.

FIG. 18 shows another embodiment of the drum 42 includes apertures 46 and a connector 48 that connects to a suction source (not shown). By applying suction to the apertures 46 of the drum 42, the epithelial disk 36 can be rolled onto the drum 42. Thereafter, the epithelial disk 36 can be removed from the drum 46 and replaced on the corneal surface 16, as described above.

Figure 19:
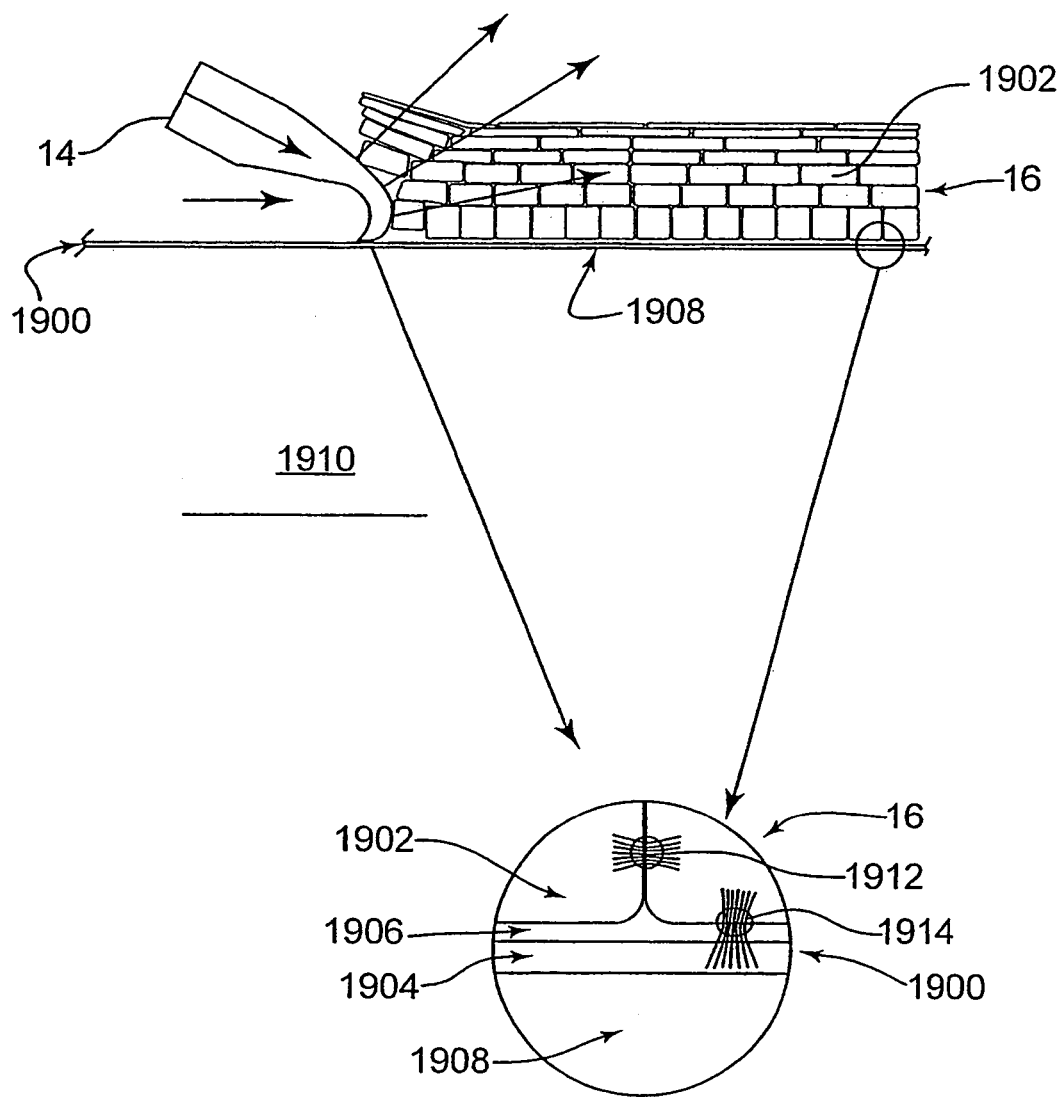
FIG. 19 is a diagram representing a side view of a separator removing the epithelial layer from the Basal membrane of the eye.

FIG. 19 is a diagram representing a side view of the separator 14 removing the epithelial layer 16 from a Basal membrane 1900 of the eye 10. The epithelial layer 16 is made up of epithelial cells 1902. The epithelial layer 16 overlies the Basal membrane 1900. The Basal membrane 1900 is formed from a lamina densa 1904 of about 50 nm in thickness and an underlying lamina lucida 1906 of about 25 nm in thickness. The lamina densa 1904 overlies a Bowman's layer 1908. The epithelial layer 16 anchors to the Bowman's layer via a complex mesh of anchoring fibrils (type VII collagen) and anchoring plaques (type VI collagen) that interact with the lamina densa 1904 and the collagen fibrils of the Bowman's layer 1908. The Bowman's layer 1908 overlies a corneal stroma 1910.

The epithelial layer 16 is stratified, possessing 5 to 6 layers of epithelial cells 1902. The epithelial layer 16 is typically about 50 to 60 micrometers in thickness. Adjacent epithelial cells 1902 are held together by desmosomes 1912. The epithelial cells 1902 are held to the underlying basal membrane 1900 by hemidesmosomes 1914 and anchoring filaments. A bottom surface of the epithelial layer 16 includes numerous microvilli and microplicae, i.e., ridges, whose glycocalyx coat interacts with, and helps to stabilize, a precorneal tear film. New epithelial cells 1902 are derived from mitotic activity in the basal membrane 1900 layer. New epithelial cells 1902 displace existing cells both superficially and centripetally.

The separator 14 includes a blunt leading edge to push the epithelial cells 1902 as the separator 14 moves across the epithelial layer 16. The separator 14 has a thickness that is preferably between one cell layer thick and the thickness of the epithelial layer 16. More preferably, the separator has a thickness between two to three cell layers in thickness. The separator 14 preferably pushes the epithelial cells 1902 and does not exert a force that could disrupt the intercellular bonds such as the desmosomes 1912. The point of separating the epithelial layer 16 has been found to often occur at the border between the lamina densa 1904 and the lamina lucida 1906. The separator 14 preferably pushes the bottom two to three layers of epithelial cells 1902 which probably contain a majority of the shear strength of the epithelial layer 16.

Figure 20:
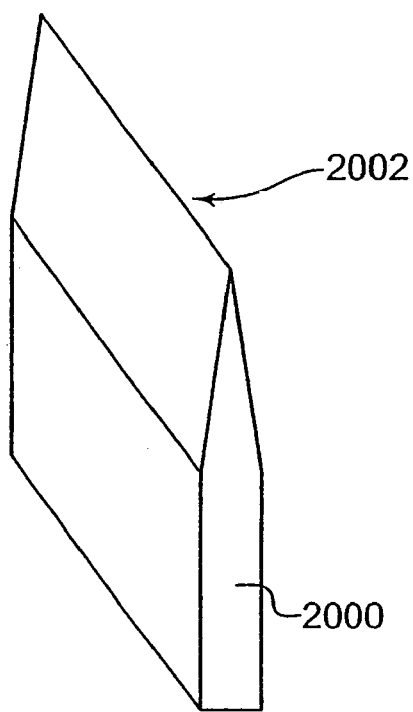
FIG. 20 is a diagram showing a perspective view of a known blade.

FIG. 20 is a diagram showing a perspective view of a known blade 2000. A leading edge 2002 of the blade 2000 is sharp and thus would not work well as a separator. The blade 2000 risks cutting the cornea.

Figure 21:
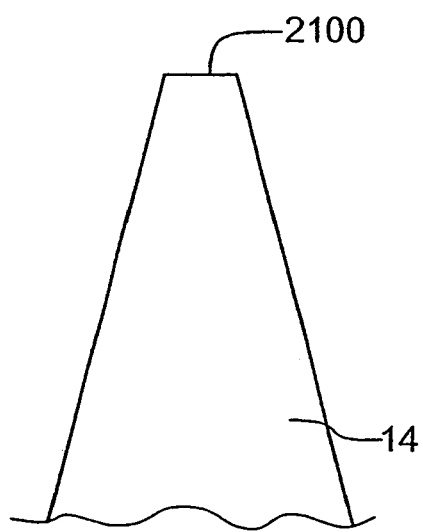
FIG. 21 is a diagram showing a side view of a separator's leading edge according to an embodiment.

FIG. 21 is a diagram showing a side view of a leading edge 2100 of a separator 14 according to an embodiment. The leading edge 2100 of the separator 14 should not be too wide such that it will reduce the consistency with which the epithelial layer 16 is penetrated. The leading edge 2100 preferably includes a 5 to 25 micrometer width, and more preferably includes about a 15 micrometers width.

Figure 22:
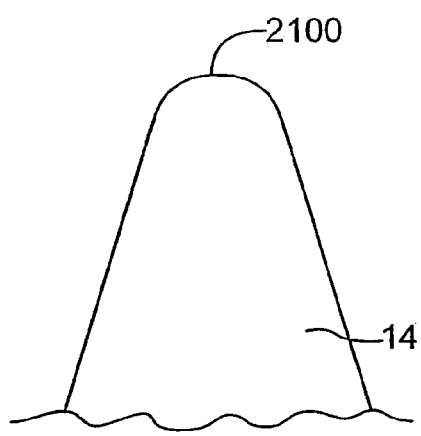
FIG. 22 is a diagram showing a side view of a separator's leading edge according to another embodiment.

FIG. 22 is a diagram showing a side view of a separator's leading edge 2100 according to another embodiment. The leading edge 2100 is rounded instead of flat.

Figure 23:
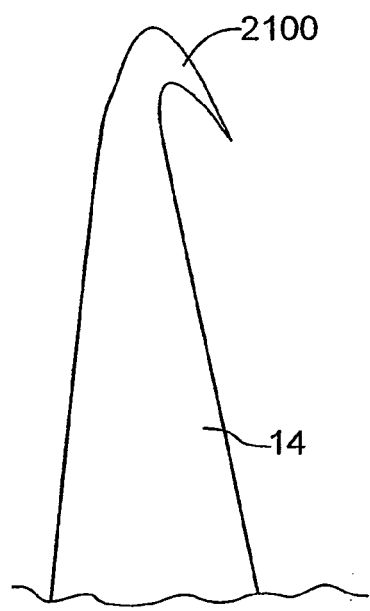
FIG. 23 is a diagram showing a side view of a separator's leading edge according to yet another embodiment.

FIG. 23 is a diagram showing a side view of a separator's leading edge 2100 according to yet another embodiment. The separator 14 is constructed, for example, by bending the leading edge 2002 of the blade 2000 shown in FIG. 20. The leading edge 2001 preferably includes a diameter of about 5 to 25 micrometers, or a radius between about 2 to 13 micrometers, and more preferably includes a diameter of 15 micrometers.

Figure 24:
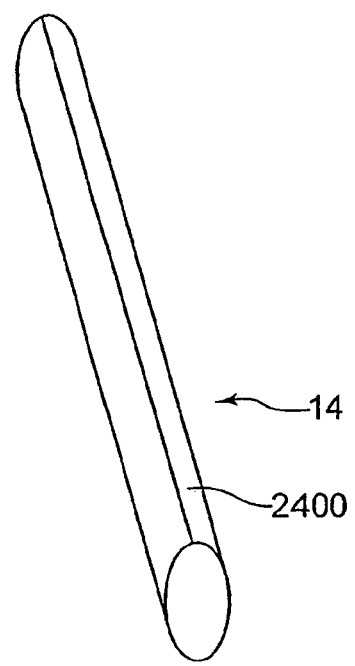
FIG. 24 is a diagram showing a perspective view of a wire that could be used as a separator according to a preferred embodiment.

FIG. 24 is a diagram showing a perspective view of a wire 2400 that could be used as the separator 14 according to a preferred embodiment. The wire 2400 includes a generally elliptical or circular cross-sectional shape. The wire 2400 includes a leading edge with a width of about 5 to 25 micrometers. The wire 2400 is preferably manufactured from a material that is strong enough to push the epithelium without breaking. Exemplary wire materials include titanium and its alloys, tungsten and its alloys, steel alloys and carbon fibers.

Figure 25:
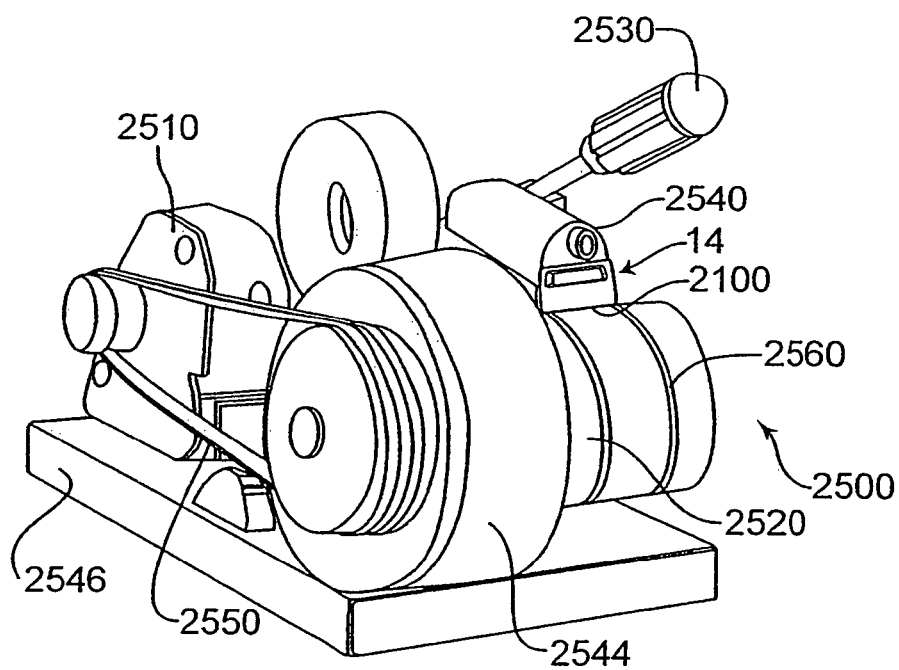
FIG. 25 shows a perspective view of an exemplary machine that is used to condition a separator according to one embodiment.

FIG. 25 shows a perspective view of an exemplary machine 2500 that is used to condition a separator 14 according to one embodiment. The machine 2500 conditions the separator 14 by changing a sharp edged separator to include a generally bent edge, for example, like the front edge of the separator 14 shown in FIG. 23.

Figure 26:
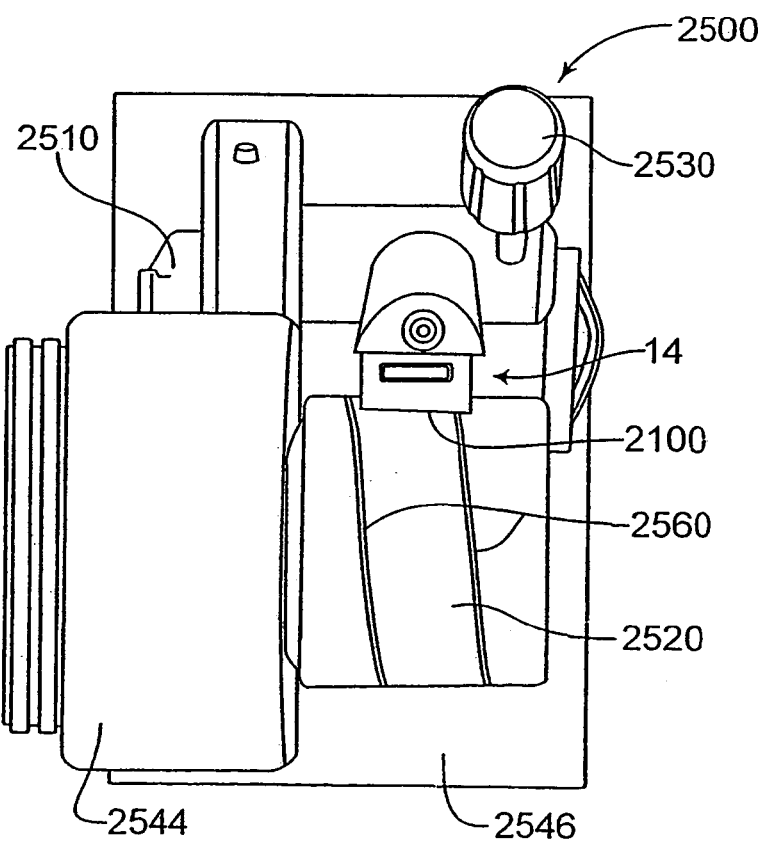
FIG. 26 shows a front view of the machine of FIG. 25 including the separator.

FIG. 26 shows a front view of the machine 2500 and separator 14. Referring to FIGS. 25 and 26, the machine 2500 includes a motor 2510, a rotating cylinder 2520, a weight 2530, or other way to hold the blade down, and a blade holder 2540. The motor 2510 and a housing 2544 of the cylinder 2520 rest on a platform 2546. The blade is held by, for example, a clamp. The blade's edge is substantially parallel to the axis of rotation of cylinder 2520. The blade's plane forms an angle between 0 and 20 degrees with the is plane defined by the axis of the cylinder 2520 and the blade's edge. The motor 2510 connects to the cylinder 2520 via a belt 2550 to rotate the cylinder 2520. In another embodiment, the motor 2510 connects directly to the cylinder 2520 to rotate the cylinder.

The cylinder 2520 includes a helical wire 2560. The helical wire 2560 and the cylinder 2520 are manufactured from steel. This helical wire serves as a helical protrusion of the rotating drum. This helix has a pitch equal to the length of the blade's edge. The helix causes only one point of the blade to be conditioned at any given moment (the point of contact between the blade's edge and the helical wire). As the helical wire 2560 rotates along with drum 2520, the point of contact travels along the blade's edge, but the amount of conditioning is equal across the blade's length. The weight 2530, and the running time and rotations of the cylinder 2520 vary the shape and width of the leading edge 2100 of the separator 14. In one embodiment, a preferred separator 14 has been conditioned by asserting 20 mN of force on the separator 14 to the cylinder 2520 and operating the cylinder for about 45 second at 0.7 (seven-tenths) rotations/second.

Figure 27:
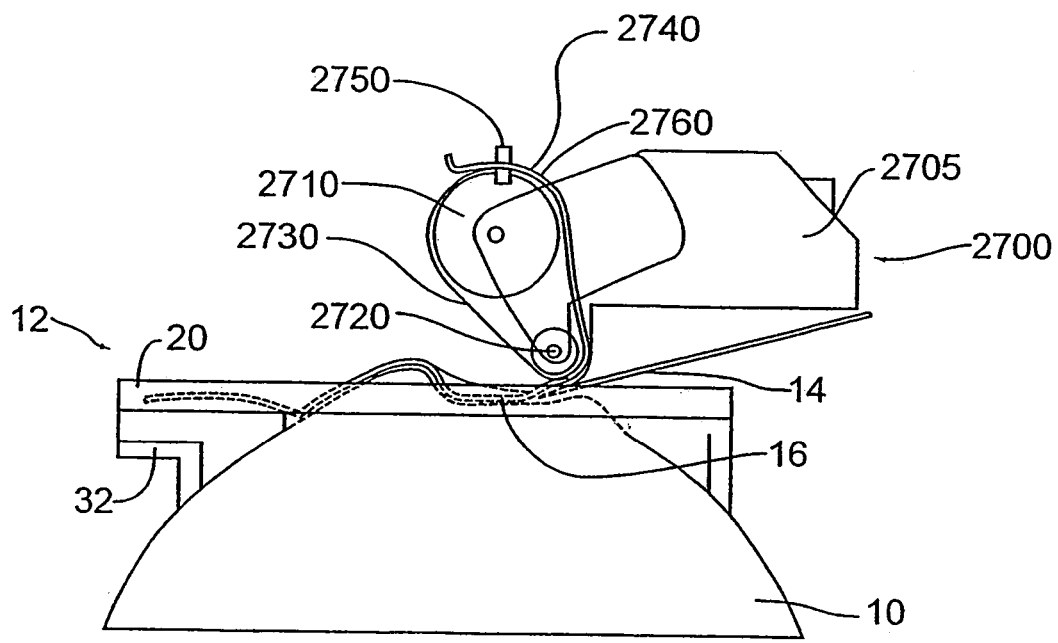
FIG. 27 shows a side view of one embodiment of a device for separating and preserving an epithelial layer.

FIG. 27 shows a side view of one embodiment of a device 2700 for separating and preserving an epithelial layer 16. The device 2700 includes a body 2705, a first drum 2720 and a second drum 2730, and a belt 2730 connecting the first drum 2720 to the second drum 2730. The device 2700 accommodates a substrate, such as film 2740. Film 2740 is used to substantially preserve the epithelial layer 16 when the epithelial layer 16 is removed from the eye 10. The film 2740 can be held to the drum 2710 with a bar or clip 2750. Alternatively, the film 2740 can serve to connect the drums 2720 and 2730 and therefore eliminate the use of belt 2730.

Figure 28:
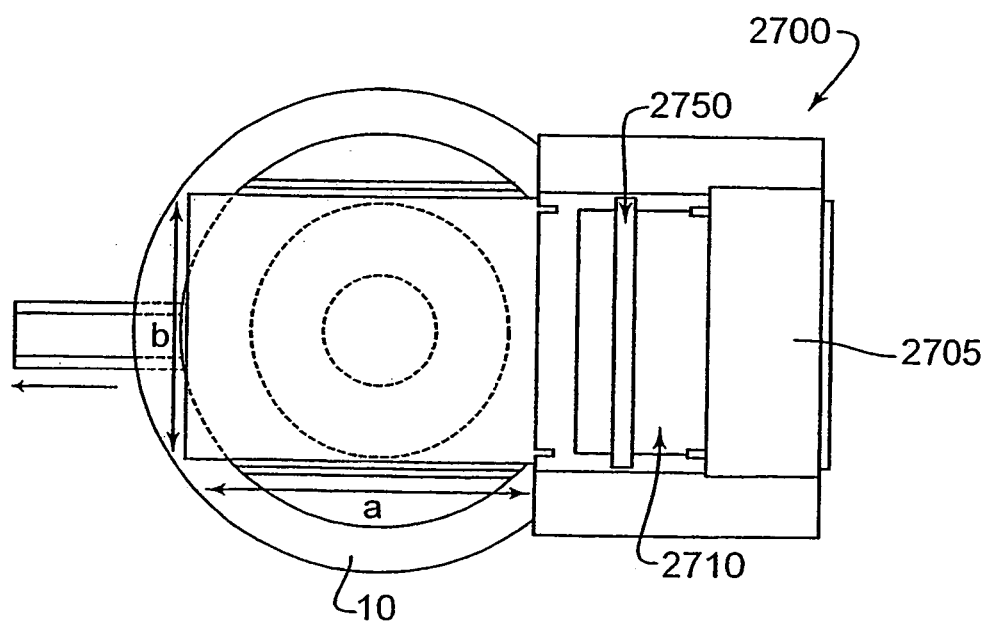
FIG. 28 shows a top view of the device of FIG. 27.

FIG. 28 shows a top view of the device 2710 and how the device 2700 is used with the clip 2750. In one embodiment, the film 2740 is rolled on to the drum 2710 and under the clip 2750 (see also FIG. 27). The first drum 2710 turns as the second drum 2720 turns since they are connected by the belt 2730. The film 2740 lays on the belt 2730 and moves as the first drum 2710 and the second drum 2720 move. The film 2740 preferably removably adheres to the belt 2730 through cohesion.

The film 2740 includes an outer surface 2760. The outer surface 2760 is constructed to adhere to the epithelial layer 16 to provide mechanical stability to the epithelial layer 16 when the epithelial layer 16 is separated from the eye 10. The film 2740 includes a natural or synthetic polymer. An exemplary polymer includes HEMA (poly-2hydroxy-ethyl-methacrylate). The film 2740 includes a thickness from about 20 to about 100 micrometers. If the film 2740 is in the shape of a strip of film, a length (a) and a width (b) of the film 2740 is preferably longer and wider than the diameter of a separated epithelium layer 16.

The film 2740 is preferably hydrated to adhere the epithelial layer 16 to the film 2740. The level of hydration of the film 2740 controls adhesion to the film 2740. The hydrated film 2740 also helps to keep cracks from forming in the removed epithelial layer 16, and to help avoid the removed epithelial layer 16 from being torn or shrinking. In one embodiment, a surface of the epithelial layer 16 is dried, for example, with a sponge or with a compressed air flow. Thereafter, the film 2740 is placed on the epithelial layer 16. The epithelial layer 16 adheres to the film 2740 because of the difference in hydration levels between the epithelial layer and the film. Thereafter, the separator 14 is used to separate the epithelial layer 16. The film 2740 and the epithelial layer 16 are rolled onto the first and second drums 2710, 2720.

It should be appreciated that the strip of film 2740 does not have to be applied with the device 2700 and that the strip does not need to include a coating. Moreover, the film 2740 can be applied before or after removal of the epithelial layer 16, and can be manually applied instead of using the device 2700.

The film 2740 can include other shapes such as the shape of a disc. A way to attach the epithelial layer 16 to a disc, such as a contact lens, is to separate the epithelial layer 16 and remove the epithelial layer 16 to the side. The epithelial layer 16 is then smoothed with a sponge and dried with the sponge, compressed air or both. Thereafter, the removed epithelial layer 16 is placed on the film 2740. The epithelial layer 16 and the film 2740 are then dried, for example, with compressed air. After about 30 seconds of drying, the epithelial layer 16 is adhered to the film 2740 and can be more easily manipulated with a reduced risk of damage.

While the invention has been described above by reference to various embodiments, it will be understood that many changes and modifications can be made without departing from the scope of the invention. It is therefore intended that the foregoing detailed description be understood as an illustration of the presently preferred embodiments of the invention, and not as a definition of the invention. It is only the following claims, including all equivalents, which are intended to define the scope of this invention.

We claim:

1. A device for separating a portion of an epithelial layer of a cornea from a corneal stroma of the cornea, the device comprising:
   means for separating the portion of the epithelial layer from the corneal stroma without substantially cutting the corneal stroma; and
   an electro-mechanical device coupled with the means for separating so as to be capable of moving the means for separating during the separating of the portion of the epithelial layer from the corneal stroma.

2. The device of claim 1 wherein the means for separating comprises a blade having a bent edge.

3. The device of claim 1 wherein the means for separating comprises a dull edge comprising a thickness configured to be between about 5 and 25 micrometers.

4. The device of claim 1 wherein the separator has a trapezoidal shape.

5. The device of claim 1 wherein the means for separating comprises a dull edge that has a dimension that is greater than about 5 mm.

6. The device of claim 1, wherein the means for separating comprises a dull edge that has a dimension that is at least as large as approximately the size of a diameter of an iris of an eye that includes the epithelial layer.

7. The device of claim 1, wherein the means for separating comprises a dull edge that has a dimension that is greater than the size of a diameter of a pupil of an eye that includes the epithelial layer.

8. The device of claim 1, further comprising an oscillation device that is capable of oscillating the means for separating as the means for separating moves across the cornea.

9. The device of claim 1, wherein the electro-mechanical device is capable of causing the means for separating to move across at least a part of the cornea and the movement is capable of causing the means for separating to separate the portion of the epithelial layer from the corneal stroma without the means for separating cutting the stroma.

10. The device of claim 1, wherein the electro-mechanical device is capable of generating through the means for separating a mechanical force that is sufficient to separate the portion of the epithelial layer from said cornea, but insufficient to cut the corneal stroma.

11. The device of claim 1, wherein the electro-mechanical device is capable of causing the means for separating to move a distance across the cornea that corresponds to at least a radius of a pupil of an eye that includes the epithelial layer so that a length of the portion of the epithelial layer corresponding to the distance is separated.

12. The device as claimed in claim 1, further comprising:
   an engagement surface; and
   wherein the electromechanical device is capable of moving the engagement surface across the cornea, and wherein during such movement the engagement surface flattens the portion of the epithelial layer.

13. The device of claim 1 wherein a dull edge of the means for separating comprises an approximately semicylindrical surface including a front edge.

14. The device of claim 13 wherein the semi-circular surface comprises a radius of between about 2 and 13 micrometers.

15. The device of claim 1 wherein a dull edge of the means for separating comprises a bent front edge to form a shape resembling a semicircle.

16. The device of claim 15 wherein the semicircle comprises a diameter of between about 5 and 25 micrometers.

17. The device of claim 1 wherein the means for separating comprises a bent blade.

18. The device of claim 17 wherein the bent blade comprises a dull edge that comprises a thickness configured to be between about 5 and 25 micrometers.

19. The device of claim 1 wherein the means for separating is unable to cut into between 20% and 80% of the cornea while the means for separating separates the portion of the epithelial layer from the corneal stroma.

20. The device of claim 19 wherein the means for separating comprises a dull edge that comprises a thickness configured to be between about 5 and 25 micrometers.

21. The device of claim 1, wherein the means for separating has a structure such that less than a 10% loss in epithelial cells of the epithelial layer results during the separation of the portion of the epithelial layer.

22. The device of claim 9, wherein the electro-mechanical device is capable of moving the means for separating along a distance of at least 6 mm, wherein the movement of the means for separating by the electro-mechanical device is capable of causing the means for separating to substantially separate the portion of the epithelial layer along the distance without substantially cutting the corneal stroma along the distance.

23. The device of claim 1, wherein the electro-mechanical device is capable of causing the dull edge to move across at least a part of the cornea as the means for separating separates the portion of the epithelial layer from the corneal stroma.

24. The device of claim 23, wherein the electro-mechanical device causes the dull edge to move a distance that corresponds to at least a radius of a pupil of an eye that includes the epithelial layer so that a length of the portion of the epithelial layer corresponding to the distance is separated.

25. The device of claim 1 further comprising a track that is capable of guiding movement of the means for separating.

26. The device of claim 25 wherein the means for separating is capable of moving along a majority of a length of the track by the electro-mechanical device such that the means for separating is capable of separating the portion of the epithelial layer for a significant portion of the length of the track and does not cut the corneal stroma along the significant portion of the length of the track.

27. The device of claim 1 wherein the means for separating has a dimension, excluding a thickness dimension, that has a magnitude that is less than about 16 mm.

28. The device of claim 27, wherein the dimension is greater than about 5 mm.

29. The device of claim 1, wherein the means for separating has a structure so as to be capable of separating the portion of the epithelial layer from said cornea without the assistance of any chemicals.

30. The device of claim 29, wherein the means for separating has a structure so as that the portion of the separated epithelial layer has an area of at least approximately $\pi * 6.25$ mm$^2$.

31. The device of claim 1 further comprising a seating.

32. The device of claim 31 further comprising a track that is capable of guiding movement of the means for separating.

33. The device of claim 32, wherein the track is associated with the seating.

34. The device of claim 32 wherein a length of the track is at least 6 mm.

35. The device of claim 32, wherein the seating or track at least partially defines an opening.

36. The device of claims 35, wherein a length of the track has a magnitude that is more than half of a dimension of the opening.

37. The device of claim 35, wherein a magnitude of a dimension of the means for separating is approximately the same as a magnitude of a dimension of the opening.

38. The device of claim 1, wherein should the means for separating contact the cornea, the electro-mechanical device would be capable of causing through the means for separating a force to sufficiently disrupt a sufficient number of bonds between the portion of the epithelial layer and the corneal stroma to allow the means for separating to separate the portion of the epithelial layer from the cornea.

39. The device of claim 38, wherein the force is not sufficient to break a substantial number of epithelial intercellular bonds associated with the portion of said epithelial layer.

40. The device of claim 38, wherein the force is not sufficient to incise a bowman's layer of the cornea.

41. A device for separating a portion of an epithelial layer of a cornea from a corneal stroma of the cornea, the device comprising:
    means for separating the epithelial layer from the corneal stroma without substantially cutting a corneal stroma of the cornea, wherein the means for separating comprises a dull edge configured to have a thickness that is greater than a thickness of one epithelial cell of the epithelial layer of the cornea; and
    an electro-mechanical device coupled with the means for separating so as to be capable of moving the means for separating during the separating of the portion of the epithelial layer.

42. The device of claim 41, wherein the dull edge is unable to substantially cut a bowman layer of the cornea while the means for separating separates the portion of the epithelial layer from the corneal stroma.

43. The device of claim 41, wherein the dull edge is unable to substantially cut a basal layer of the cornea while the means for separating separates the portion of the epithelial layer from the corneal stroma.

44. The device of claim 41 wherein the dull edge has a dullness such that it is unable to cut into between 20% and 80% of the cornea while the means for separating separates the portion of the epithelial layer from the corneal stroma.

45. The device of claim 41, wherein the electro-mechanical device is capable of causing the dull edge to move across at least a part of the cornea as the means for separating separates the portion of the epithelial layer from the corneal stroma.

46. The device of claim 41 wherein the dull edge has a dimension that is greater than about 5 mm.

47. The device of claim 41, wherein the dull edge has a dimension that is at least as large as approximately the size of a diameter of an iris of an eye that includes the epithelial layer.

48. The device of claim 41, wherein the dull edge has a dimension that is greater than the size of a diameter of a pupil of an eye that includes the epithelial layer.

49. The device of claim 41, further comprising an oscillation device that is capable of oscillating the dull edge as the dull edge moves across the cornea.

50. The device of claim 41, wherein the electro-mechanical device is capable of generating through the means for separating a mechanical force that is sufficient to separate the portion of the epithelial layer from the cornea, but insufficient to cut the corneal stroma.

51. The device of claim 41, wherein the electro-mechanical device is capable of causing the dull edge to move a distance across the cornea that corresponds to at least a radius of a pupil of an eye that includes the epithelial layer so that a length of the portion of the epithelial layer corresponding to the distance is separated.

52. The device as claimed in claim 41, further comprising:
an engagement surface; and
wherein the electro-mechanical device is capable of moving the engagement surface across the cornea, wherein during such movement the engagement surface flattens the portion of the epithelial layer.

53. The device of claim 41, wherein the dull edge moves across at least a part of the cornea as the means for separating separates the portion of the epithelial layer from the corneal stroma.

54. The device of claim 53, wherein the electro-mechanical device is capable of causing the dull edge to move a distance that corresponds to at least a radius of a pupil of an eye that includes the epithelial layer so that a length of the portion of the epithelial layer corresponding to the distance is separated.

55. The device of claim 41 further comprising a track that is capable of guiding movement of the dull edge.

56. The device of claim 55 wherein the electro-mechanical device is capable of moving the means for separating so that the means for separating is movable along a majority of a length of the track wherein the means for separating does not cut the corneal stroma anywhere along the majority of the length of the track.

57. The device of claim 41 wherein excluding a thickness dimension, the dull edge has a dimension that has a magnitude that is less than about 16 mm.

58. The device of claim 57, wherein the dimension is greater than about 5 mm.

59. The device of claim 41, wherein the edge has a structure so as to be capable of separating the portion of the epithelial layer from the cornea without the assistance of any chemicals.

60. The device of claim 59, wherein the edge has a structure so that the separated portion of the epithelial layer has an area of at least approximately $\pi*6.25$ mm$^2$.

61. The device of claim 41, wherein the electro-mechanical device is capable of causing the means for separating to move across at least a part of the cornea as the means for separating separates the portion of the epithelial layer from the corneal stroma.

62. The device of claim 61, wherein the electro-mechanical device is capable of moving the means for separating along a distance of at least 6 mm, wherein the means for separating is capable of separating the portion of the epithelial layer and does not cut the corneal stroma while moving along the distance.

63. The device of claim 41, wherein the means for separating has a structure such that less than a 10% loss in epithelial cells of the epithelial layer results during the separation of the portion of the epithelial layer.

64. The device of claim 63, wherein the dull edge is unable to substantially cut a bowman layer of the cornea while the means for separating separates the portion of the epithelial layer from the corneal stroma.

65. The device of claim 63, wherein the dull edge is unable to substantially cut a basal layer of the cornea while the means for separating separates the portion of the epithelial layer from the corneal stroma.

66. The device of claim 41, wherein at least a portion of the dull edge contacts a surface of the cornea from which the portion of the epithelial layer is separated as the means for separating moves across the cornea during the separation.

67. The device of claim 41 wherein the means for separating has a structure such that the means for separating is capable of lifting the portion of the epithelial layer and capable of separating the portion of the epithelial layer from the corneal stroma.

68. The device of claim 67 wherein the means for separating is capable of applying at least one mechanical force under at least one cell layer of the portion of the epithelial layer in order to lift the portion of the epithelial layer.

69. The device of claim 67, wherein the dull edge is unable to substantially cut a bowman layer of the cornea while the means for separating separates the portion of the epithelial layer from the corneal stroma.

70. The device of claim 67, wherein the dull edge is unable to substantially cut a basal layer of the cornea while the means for separating separates the portion of the epithelial layer from the corneal stroma.

71. The device of claim 67, wherein the means for separating has a structure such that less than a 10% loss in epithelial cells of the portion of the epithelial layer results during the separation of the portion of the epithelial layer.

72. The device of claim 67, wherein the means for separating further comprises a surface directly attached to the dull edge.

73. The device of claim 72, wherein the surface and the dull edge meet so as to define an angled corner.

74. The device of claim 73 wherein the means for separating is capable of applying at least one mechanical force under at least one cell layer of the portion of the epithelial layer in order to lift the portion of the epithelial layer.

75. The device of claim 73 wherein the means for separating is capable of applying at least one mechanical force to a portion of the cornea during the separating of the portion of the epithelial layer.

76. The device of claim 73, wherein at least a portion of the dull edge contacts a surface of the cornea from which the portion of the epithelial layer is separated as the means for separating mover across the cornea during the separation.

77. The device of claim 73, wherein the means for separating further comprises a second surface directly attached to the dull edge, wherein the dull edge is positioned between the surface and the second surface.

78. The device of claim 77 wherein the means for separating is capable of applying at least one mechanical force under at least one cell layer of the portion of the epithelial layer in order to lift the portion of the epithelial layer.

79. The device of claim 78, wherein contact between the means for separating and the epithelial layer generates the at least one mechanical force that solely causes the portion of the epithelial layer to separate from the corneal stroma.

80. The device of claim 78, wherein the mechanical force is by direct contact between the means for separating and the at least one cell below an outermost layer of the epithelial layer.

81. The device of claim 78, wherein the at least one mechanical force has a vector component pointing towards the cornea.

82. The device of claim 77 wherein the means for separating is capable of applying at least one mechanical force to a portion of the cornea during the separating of the portion of the epithelial layer.

83. The device of claim 82, wherein contact between the means for separating and the epithelial layer generates the at least one mechanical force that solely causes the portion of the epithelial layer to separate from the corneal stroma.

84. The device of claim 82, wherein the at least one mechanical force has a vector component pointing towards the cornea.

85. The device of claim 77, wherein the surface and the dull edge meet so as to define an angled corner and the second surface and the dull edge meet so as to define a second angled corner.

86. The device of claim 85 wherein the means for separating applies at least one mechanical force under at least one cell layer of the portion of the epithelial layer in order to lift the portion of the epithelial layer.

87. The device of claim 85 wherein the means for separating applies at least one mechanical force to a portion of the cornea during the separating of the portion of the epithelial layer.

88. The device of claim 41 further comprising a seating.

89. The device of claim 88 further comprising a track that is capable of guiding movement of the dull edge.

90. The device of claim 89, wherein the track is associated with the seating.

91. The device of claim 89 wherein a length of the track is at least 6 mm.

92. The device of claim 89, wherein the seating or track at least partially defines an opening.

93. The device of claims 92, wherein a length of the track has a magnitude that is more than half of a dimension of the opening.

94. The device of claim 92, wherein a magnitude of a dimension of the dull edge is approximately the same as a magnitude of a dimension of the opening.

95. The device of claim 41, wherein should the means for separating contact the cornea, the electro-mechanical device would be capable of causing through the means for separating a force to sufficiently disrupt a sufficient number of bonds between the portion of said epithelial layer and the corneal stroma to allow said means for separating to separate the portion of the epithelial layer from the said cornea.

96. The device of claim 95, wherein the force is not sufficient to break a substantial number of epithelial intercellular bonds associated with the portion of said epithelial layer.

97. The device of claim 95, wherein the force is not sufficient to incise a bowman's layer of the cornea.

98. A device for separating a portion of an epithelial layer of a cornea from a corneal stroma of the cornea, the device comprising:
   means for separating the epithelial layer from the corneal stroma without substantially cutting a corneal stroma of the cornea, wherein the means for separating comprises a dull edge configured to have a thickness that is less than a total thickness of an epithelial layer; and
   an electro-mechanical device coupled with the means for separating so as to be capable of moving the means for separating during the separating of the portion of the epithelial layer.

99. The device of claim 98, wherein the dull edge is unable to substantially cut a bowman layer of the cornea while the means for separating separates the portion of the epithehal layer from the corneal stroma.

100. The device of claim 98, wherein the dull edge is unable to substantially cut a basal layer of the cornea while the means for separating separates the portion of the epithelial layer from the corneal stroma.

101. The device of claim 98 wherein the dull edge has a dullness such that it is unable to cut into between 20% and 80% of the cornea while the means for separating separates the portion of the epithelial layer from the corneal stroma.

102. The device of claim 98, wherein at least a portion of the dull edge contacts a surface of the cornea from which the portion of the epithelial layer is separated as the means for seperating moves across the cornea during the separation.

103. The device of claim 98 wherein the edge has a dimension that is greater than about 5 mm.

104. The device of claim 98, wherein the dull edge has a dimension that is at least as large as approximately the size of a diameter of an iris of an eye that includes the epithelial layer.

105. The device of claim 98, wherein the dull edge has a dimension that is greater than the size of a diameter of a pupil of an eye that includes the epithelial layer.

106. The device of claim 98, further comprising an oscillation device that is capable of oscillating the dull edge as the dull edge moves across the cornea.

107. The device of claim 98, wherein the electro-mechanical device is capable of generating through the means for separating a mechanical force that is sufficient to separate the portion of the epithelial layer from the cornea, but insufficient to cut the corneal stroma.

108. The device of claim 98, wherein the electro-mechanical device is capable of causing the means for separating to move a distance across the cornea that corresponds to at least a radius of a pupil of an eye that includes the epithelial layer so that a length of the portion of the epithelial layer substantially corresponding to the distance is separated.

109. The device as claimed in claim 98, further comprising:
   an engagement surface; and
   wherein the electro-mechanical device is capable of moving the engagement surface across the cornea, wherein during such movement the engagement surface flattens the portion of the epithelial layer.

110. The device of claim 98, wherein the means for separating has a structure such that less than a 10% loss in epithelial cells of the epithelial layer results during the separation of the portion of the epithelial layer.

111. The device of claim 110, wherein the dull edge is unable to substantially cut a bowman layer of the cornea while the means for separating separates the portion of the epithelial layer from the corneal stroma.

112. The device of claim 110, wherein the dull edge is unable to substantially cut a basal layer of the cornea while the means for separating separates the portion of the epithelial layer from the corneal stroma.

113. The device of claim 98 wherein the means for separating has a structure such that the means for separating is capable of lifting the portion of the epithelial layer during the separating of the portion of the epithelial layer.

114. The device of claim 113 wherein the means for separating is capable of applying at least one mechanical force under at least one cell layer of the portion of the epithelial layer in order to lift the portion of the epithelial layer.

115. The device of claim 113, wherein the dull edge is unable to substantially cut a bowman layer of the cornea while the means for separating separates the portion of the epithelial layer from the corneal stroma.

116. The device of claim 113, wherein the dull edge is unable to substantially cut a basal layer of the cornea while the means for separating separates the portion of the epithelial layer from the corneal stroma.

117. The device of claim 113, wherein the means for separating has a structure such that less than a 10% loss in epithelial cells of the portion of the epithelial layer results during the separation of the portion of the epithelial layer.

118. The device of claim 113, wherein the means for separating further comprises a surface directly attached to the dull edge.

119. The device of claim 118, wherein the surface and the dull edge meet so as to define an angled corner.

120. The device of claim 119 wherein the means for separating is capable of applying at least one mechanical force under at least one cell layer of the portion of the epithelial layer in order to lift the portion of the epithelial layer.

121. The device of claim 119 wherein the means for separating is capable of applying at least one mechanical force to a portion of the cornea during the separating of the portion of the epithelial layer.

122. The device of claim 119, wherein the means for separating further comprises a second surface directly attached to the dull edge, wherein the dull edge is positioned between the surface and the second surface.

123. The device of claim 122, wherein at least a portion of the dull edge contacts a surface of the cornea from which the portion of the epithelial layer is separated as the means for separating moves across the cornea during the separation.

124. The device of claim 122 wherein the means for separating is capable of applying at least one mechanical force under at least one cell of the portion of the epithelial layer in order to lift the portion of the epithelial layer.

125. The device of claim 124, wherein contact between the means for separating and the epithelial layer generates the at least one mechanical force that solely causes the portion of the epithelial layer to separate from the corneal stroma.

126. The device of claim 124, wherein the at least one mechanical force is by direct contact between the means for separating and the at least one cell layer below an outermost layer of the epithelial layer.

127. The device of claim 124, wherein the at least one mechanical force has a vector component pointing towards the cornea.

128. The device of claim 122 wherein the means for separating is capable of applying at least one mechanical force to a portion of the cornea during the separating of the portion of the epithelial layer.

129. The device of claim 128, wherein contact between the means for separating and the epithelial layer generates the at least one mechanical force that solely causes the portion of the epithelial layer to separate from the corneal stroma.

130. The device of claim 128, wherein the at least one mechanical force has a vector component pointing towards the cornea.

131. The device of claim 122, wherein the surface and the dull edge meet so as to define an angled corner and the second surface and the dull edge meet so as to define a second angled corner.

132. The device of claim 131 wherein the means for separating applies at least one mechanical force under at least one cell layer of the portion of the epithelial layer in order to lift the portion of the epithelial layer.

133. The device of claim 131 wherein the means for separating applies at least one mechanical force to a portion of the cornea during the separating of the portion of the epithelial layer.

134. The device of claim 98, wherein the dull edge moves across at least a part of the cornea as the means for separating separates the portion of the epithelial layer from the corneal stroma.

135. The device of claim 134, wherein the electro-mechanical device is capable of causing the dull edge to move a distance across the cornea that corresponds to at least a radius of a pupil of an eye that includes the epithelial layer so that a length of the portion of the epithelial layer corresponding to the distance is separated.

136. The device of claim 98 further comprising a track that is capable of guiding movement of the dull edge.

137. The device of claim 136 wherein the electro-mechanical device is capable of moving the means for separating so that the means for separating is movable along a majority of a length of the track wherein the means for separating does not cut the corneal stroma anywhere along the majority of the length of the track.

138. The device of claim 98 further comprising a seating.

139. The device of claim 138 further comprising a track that is capable of guiding movement of the dull edge.

140. The device of claim 139, wherein the track is associated with the seating.

141. The device of claim 139 wherein a length of the track is at least 6 mm.

142. The device of claim 139, wherein a magnitude of a dimension of the dull edge is approximately the same as a magnitude of a dimension of the opening.

143. The device of claim 139, wherein the seating or track at least partially defines an opening.

144. The device of claims 143, wherein a length of the track has a magnitude that is more than half of a dimension of the opening.

145. The device of claim 98 wherein excluding a thickness dimension, the edge has a dimension that has a magnitude that is less than about 16 mm.

146. The device of claim 145, wherein the dimension is greater than about 5 mm.

147. The device of claim 98, wherein should the means for separating contact the cornea, the electro-mechanical device would be capable of causing through the means for separating a force to sufficiently disrupt a sufficient number of bonds between the portion of the epithelial layer and the cornea to allow the means for separating to separate the portion of said epithelial layer from the cornea.

148. The device of claim 147, wherein the force is not sufficient to break a substantial number of epithelial intercellular bonds associated with the portion of said epithelial layer.

149. The device of claim 147, wherein the force is not sufficient to incise a bowman's layer of the cornea.

150. The device of claim 98, wherein the edge has a structure so as to be capable of separating the portion of the epithelial layer from the cornea without the assistance of any chemicals.

151. The device of claim 150, wherein the edge has a structure so that the separated portion of the epithelial layer has an area of at least approximately $\pi*6.25$ mm$^2$.

152. The device of claim 98, wherein the electro-mechanical device is capable of causing the means for separating to move across at least a part of the cornea as the means for separating separates the portion of the epithelial layer from the corneal stroma.

153. The device of claim 152, wherein the electro-mechanical device is capable of moving the means for separating along a distance of at least 6 mm, wherein the means for separating is capable of separating the portion of the epithelial layer and does not cut the corneal stroma while moving along the distance.

154. A device for separating a portion of an epithelial layer of a cornea from a corneal stroma of the cornea, the device comprising:

means for separating the portion of the epithelial layer from a corneal stroma without the use of chemicals and without substantially cutting the corneal stroma of the cornea along a predetermined path, wherein the means for separating comprises a dull edge configured to have a thickness that is greater than a thickness of one epithelial cell of the epithelial layer of the cornea and is less than a total thickness of the epithelial layer; and means for moving the means for separating and for constraining movement of the means for separating along the predetermined path.

155. The device of claim 154, wherein the means for moving is capable of causing the dull edge to move a distance along the predetermined path that corresponds to at least a radius of a pupil of an eye that includes the epithelial layer so that a length of the portion of the epithelial layer corresponding to the distance is separated.

156. The device of claim 154, wherein the means for moving is capable of generating through the means for separating a mechanical force that is sufficient to separate the portion of the epithelial layer from said cornea, but insufficient to cut said corneal stroma.

157. The device as claimed in claim 154, further comprising:

an engagement surface, wherein the means for moving is capable of moving the engagement surface and during movement of the engagement surface the engagement surface flattens the portion of the epithelial layer.

158. A device for separating a portion of an epithelial layer of a cornea from a corneal stroma of the cornea, the device comprising:

means for separating the portion of the epithelial layer from a corneal stroma without substantially cutting the corneal stroma of the cornea along a path having a length of at least a radius of a pupil of an eye that includes the epithelial layer; and means for moving the means for separating and for constraining movement of the means for separating along the path;

wherein a dimension of the portion mostly corresponds to the length.

159. The device as claimed in claim 158, further comprising:

an engagement surface, wherein the means for moving is capable of moving the engagement surface and during movement of the engagement surface the engagement surface flattens the portion of the epithelial layer.

160. A device for separating a portion of an epithelial layer of a cornea from a corneal stroma of the cornea, the device comprising:

means for separating the portion of the epithelial layer from the corneal stroma without the use of chemicals and without substantially cutting a corneal stroma of the cornea, wherein the means for separating comprises a dull edge configured to have a thickness that is greater than a thickness of one epithelial cell of the epithelial layer of the cornea and is less than a total thickness of the epithelial layer;

means for moving the means for separating and for constraining movement of the means for separating along a predetermined path; and means for positioning the means for separating relative to the cornea.

161. The device of claim 160, wherein the means for moving is capable of causing the dull edge to move a distance along the predetermined path that corresponds to at least a diameter of a pupil of an eye that includes the epithelial layer.

162. The device of claim 160, wherein the means for moving is capable of generating through the means for separating a mechanical force that is sufficient to separate the portion of the epithelial layer from the cornea, but insufficient to cut the corneal stroma.

163. The device as claimed in claim 160, further comprising:

an engagement surface, wherein the means for moving is capable of moving the engagement surface and during movement of the engagement surface the engagement surface flattens the portion of the epithelial layer.

164. A device for separating a portion of an epithelial layer of a cornea from a corneal stroma of the cornea, the device comprising:

means for separating the portion of the epithelial layer from the corneal stroma without substantially cutting into a corneal stroma of the cornea, wherein the means for separating comprises a dull edge that has a thickness configured to be greater than a thickness of one epithelial cell of the epithelial layer of the cornea and is less than a total thickness of the epithelial layer;

means for moving the means for separating and guiding movement of the means for separating along a predetermined path; and means for positioning the means for separating relative to the cornea.

165. The device of claim 164, wherein the means for moving is capable of causing the dull edge to move a distance along the predetermined path that corresponds to at least a diameter of a pupil of an eye that includes the epithelial layer.

166. The device of claim 164, wherein the means for moving is capable of generating though the means for separating a mechanical force that is sufficient to separate the epithelial layer from the cornea, but insufficient to cut the corneal stroma.

167. The device as claimed in claim 164, further comprising:

an engagement surface, wherein the means for moving is capable of moving the engagement surface and during movement of the engagement surface the engagement surface flattens the portion of the epithelial layer.

* * * * *

UNITED STATES PATENT AND TRADEMARK OFFICE
CERTIFICATE OF CORRECTION

PATENT NO. : 7,004,953 B2
APPLICATION NO. : 10/098167
DATED : February 28, 2006
INVENTOR(S) : Ioannis Pallikaris et al.

Page 1 of 1

It is certified that error appears in the above-identified patent and that said Letters Patent is hereby corrected as shown below:

<u>On the Title Page item (56), under U.S. Patent Documents</u>

On page 2, Column 2, line 47, after "12/2003" delete "Yee et al." and substitute --Somani et al.--.

Column 9, in claim 14, line 1; delete "semi-circular" and substitute --semi-cylindrical-- in its place.

Column 12, in claim 76, line 4, delete "mover" and substitute --moves-- in its place.

Signed and Sealed this

Twentieth Day of March, 2007

JON W. DUDAS
*Director of the United States Patent and Trademark Office*